(12) United States Patent
Neff et al.

(10) Patent No.: US 9,102,721 B2
(45) Date of Patent: Aug. 11, 2015

(54) THERAPEUTIC METHOD

(75) Inventors: Thomas B. Neff, Atherton, CA (US);
Seth Porter, San Carlos, CA (US);
Frank H. Valone, Mill Valley, CA (US)

(73) Assignee: FibRoGen, Inc., San Francisco, CA (US)

( * ) Notice: Subject to any disclaimer, the term of this patent is extended or adjusted under 35 U.S.C. 154(b) by 0 days.

(21) Appl. No.: 13/980,806

(22) PCT Filed: Jan. 23, 2012

(86) PCT No.: PCT/US2012/222263
§ 371 (c)(1),
(2), (4) Date: Jan. 17, 2014

(87) PCT Pub. No.: WO2012/100262
PCT Pub. Date: Jul. 26, 2012

(65) Prior Publication Data
US 2014/0127224 A1 May 8, 2014

Related U.S. Application Data

(60) Provisional application No. 61/461,663, filed on Jan. 21, 2011.

(51) Int. Cl.
*A61K 39/395* (2006.01)
*C07K 16/22* (2006.01)
*A61K 31/517* (2006.01)
*A61K 31/7068* (2006.01)
*A61K 45/06* (2006.01)
*A61K 39/00* (2006.01)

(52) U.S. Cl.
CPC ............... *C07K 16/22* (2013.01); *A61K 31/517* (2013.01); *A61K 31/7068* (2013.01); *A61K 39/39558* (2013.01); *A61K 45/06* (2013.01); *A61K 2039/505* (2013.01)

(58) Field of Classification Search
None
See application file for complete search history.

(56) References Cited

U.S. PATENT DOCUMENTS

| 5,770,209 | A | 6/1998 | Grotendorst et al. |
| 6,492,129 | B1 | 12/2002 | Grotendorst |
| 7,115,390 | B1 | 10/2006 | Grotendorst et al. |
| 7,405,274 | B2 * | 7/2008 | Lin et al. ............... 530/387.1 |
| 7,871,617 | B2 * | 1/2011 | Lin et al. ............... 424/139.1 |
| 2003/0113816 | A1 | 6/2003 | Weitz et al. |
| 2004/0248206 | A1 | 12/2004 | Lin et al. |
| 2005/0271670 | A1 | 12/2005 | Spong et al. |
| 2008/0206256 | A1 * | 8/2008 | Spong et al. ............ 424/145.1 |
| 2010/0223680 | A1 * | 9/2010 | Kan et al. ................ 800/10 |

FOREIGN PATENT DOCUMENTS

| EP | 1043335 | 10/2000 |
| WO | WO 2010/119991 A2 | 10/2010 |

OTHER PUBLICATIONS

Adler SG: "Phase 1 study of anti-CTGF monoclonal antibody in patients with diabetes and microalbuminuria." Clin J Am Soc Nephrol. Aug. 2010;5(8):1420-8.

Aikawa T: "Connective tissue growth factor-specific antibody attenuates tumor growth, metastasis and angiogenesis in an orthotopic mouse model of pancreatic cancer." Mol Cancer Ther, May 2006: 5(5):1108-16.

Bennewith KL: "The Role of Tumor Cell—Derived Connective Tissue Growth Factor (CTGF/CCN2) in Pancreatic Tumor Growth." Cancer Res. Feb. 1, 2009;69(3):775-84.

Dornhofer N: "Connective tissue growth factor-specific monoclonal antibody therapy inhibits pancreatic tumor growth and metastasis." Cancer Res, Jun. 2006: 66(11):5816-27.

Karger A: "Molecular insights into connective tissue growth factor action in rat pancreatic stellate cells." Cell Signal. Oct. 2008;20(10):1865-72.

Kwon S: "Expression of connective tissue growth factor in pancreatic cancer cell lines," Int J Oncol. Oct. 2007;31(4):693-703.

Lieber M: Establishment of a continuous tumor-cell line (panc-1) from a human carcinoma of the exocrine pancreas. Int J Cancer. May 15, 1975;15(5):741-7.

Wenger C: Expression and differential regulation of connective tissue growth factor in pancreatic cancer cells. Oncogene. Jan. 28, 1999;18(4):1073-80.

* cited by examiner

*Primary Examiner* — Marianne P Allen

(57) ABSTRACT

Described herein are methods for treating connective tissue growth factor (CTGF)-associated cancers, including pancreatic cancer, using an anti-CTGF antibody. Increased antibody exposure was demonstrated to improve patient outcome.

3 Claims, 2 Drawing Sheets

THERAPEUTIC METHOD

FIELD OF THE INVENTION

The present invention relates to methods useful for treating connective tissue growth factor (CTGF)-associated cancers, particularly pancreatic cancer. Improved methods and regimens for the administration of anti-CTGF antibodies and other therapeutic agents are provided.

BACKGROUND OF THE INVENTION

CTGF-associated cancers include more common forms of cancer such as breast and colon cancer and also some of the most deadly such as pancreatic cancer and gliomas, including glioblastomas. Pancreatic cancer claims the lives of approximately 35,000 individuals in the US every year. Incidence rates are similar to mortality rates. Frequently, a diagnosis of pancreatic cancer is made at an advanced stage that precludes surgical excision of tumor masses. Treatment with the chemotherapy agent gemcitabine, used alone or in combination with other drugs, is the standard of care, but, despite therapy, patients survive only about 6 months from time of diagnosis. In the absence of treatment, the survival time is only 2 to 4 months.

The role of CTGF as the central mediator of tissue remodeling and fibrosis (persistent and excessive scarring) is well established in the scientific literature. Several recent studies also implicate CTGF in tumor progression, including tumor cell survival and metastasis. CTGF promotes epithelial to mesenchymal transition (EMT), a process whereby normal epithelial cells become migratory, matrix-producing fibroblasts that have been shown to be important during invasion and metastasis (Burns W C, et al. *J Am Soc Nephrol.* 2006 September; 17(9):2484-94; Yang J and Weinberg R A. *Dev Cell.* 2008 June; 14(6):818-29)). Elevated CTGF levels are found in desmoplastic cancers, where CTGF may induce and support the formation of the extensive fibrous connective tissue (desmoplasia) around the cancer. The cells in the dense tissue capsule, such as myofibroblasts and stellate cells, may further support tumor growth through the secretion of growth factors including CTGF and also through the shielding the tumor from chemotherapy agents. Desmoplastic cancers include pancreatic, breast, glioblastoma, and sarcomas (Wenger, C, et al. *Oncogene* 1999; 18:1073-1080; Ryu, B., et al. *Cancer Res.* 2001; 61:1833-1838; Iacobuzio-Donahue C. A., et al. *Am J Pathol.* 2002 January; 16(1):91-9).

Results from nonclinical models of pancreatic cancer demonstrate that blocking the expression or activity of CTGF reduces tumor growth and metastasis (Aikawa T, et al. *Mol. Cancer Ther.* 2006 May; 5(5):1108-16; Dornhöfer N, et al. *Cancer Res.* 2006; 66:5817-27; Bennewith K, et al. *Cancer Res.* 2009; 69:775-784; U.S. Application Publication No. US2005/0271670). Given the intractable nature of pancreatic and other CTGF-associated cancers, therapies that directly intervene with the expression or activity of CTGF are needed. The treatment methodologies and regimens disclosed herein address this need.

SUMMARY OF THE INVENTION

The present invention provides for improved methods and regimens for the administration of anti-CTGF antibodies that are useful in the treatment of CTGF-associated cancers, including pancreatic cancers.

In one aspect of the invention, a method is provide for treating pancreatic cancer in a subject, the method comprising administering to the subject a sufficient quantity of an anti-CTGF antibody to achieve a $C_{min}$ of at least 75 µg/ml in blood.

In another aspect of the invention, a method is provide for treating pancreatic cancer in a subject, the method comprising administering to the subject a sufficient quantity of an anti-CTGF antibody to achieve an antibody exposure expressed as the area under the curve 0-14 days (AUC0-14) of at least 80,000 µg*h/ml.

In a further aspect of the invention, a method is provided for treating pancreatic cancer in a subject, the method comprising administering a sufficient quantity of an anti-CTGF antibody to achieve a $C_{min}/m^2$ of at least 50 µg/ml/m².

In an additional aspect of the invention, a method is provided for treating pancreatic cancer in a subject, the method comprising administering at least 3.0 g of an anti-CTGF antibody in a treatment cycle.

In another aspect of the invention, a method is provided for treating pancreatic cancer in a subject, the method comprising administering at least 15 mg/kg of an anti-CTGF antibody in a treatment cycle.

In a still further aspect of the invention, a method is provided for treating pancreatic cancer in a subject, the method comprising administering at least 500 mg/m² of an anti-CTGF antibody in a treatment cycle.

In a further aspect the invention provides a method for treating pancreatic cancer in a subject comprising a) administering a first dose of an anti-CTGF antibody; b) measuring a first blood level of the antibody in the patient; c) comparing the first blood level of the antibody against a first target antibody blood level; and d) administering a second dose of the antibody calculated to achieve or exceed the first target antibody blood level. In some embodiments, the pancreatic cancer is an adenocarcinoma. In other embodiments, the pancreatic cancer is a ductal adenocarcinoma.

In some embodiments, the anti-CTGF antibody is a monoclonal antibody or a fragment thereof that specifically binds to CTGF. In further embodiments, the anti-CTGF antibody is CLN-1 (also called CLN1) or a derivative thereof that specifically binds to CTGF. In some embodiments, the first dose of the antibody is at least 500 mg/m². In some embodiments, the first dose of the antibody is at least 15 mg/kg.

In some embodiments, the first blood level of the antibody in the patient is measured at least 7 days post-administration. In other embodiments, the first blood level is measured about 8, 9, 10, 11, 12, 13, 14, 15, 16, 17, 18, 19, 20, or 21 days post-administration. In some embodiments, the first target antibody blood level is at least 50 µg/ml, 75 µg/ml, 100 µg/ml, 125 µg/ml, 150 µg/ml, 200 µg/ml, 250 µg/ml, 300 µg/ml, 400 µg/ml or 500 µg/ml. In some embodiments, the method further comprises measuring a second blood level of the antibody in the patient after the second administration. In other embodiments, the method further comprises comparing the second blood level of the antibody after the second administration to a second target antibody blood level. In further embodiments, the method further comprises administering a third dose of the antibody calculated to achieve or exceed the second target antibody blood level.

In some embodiments, the second target antibody blood level is at least 50 µg/ml, 75 µg/ml, 100 µg/ml, 125 µg/ml, 150 µg/ml, 200 µg/ml, 250 µg/ml, 300 µg/ml, 400 µg/ml or 500 µg/ml. In other embodiments, the second target antibody blood level is higher than the first target blood level. In further embodiments, the method further comprises administering to the subject a therapeutically effective amount of a chemotherapy agent. In some embodiments, the chemotherapy agent is gemcitabine or erlotinib.

In another aspect of the invention, a method is provided for treating pancreatic cancer in a subject comprising a) administering a first dose of an anti-CTGF antibody; b) measuring a first antibody blood level in the patient; and c) administering a second dose of the antibody calculated to achieve or exceed a second antibody blood level that is higher than the first antibody blood level when measured after substantially the same time interval post-administration as the first antibody blood level.

In one aspect of the invention, a method is provided for treating pancreatic cancer in a subject comprising administering in one treatment cycle at least 1.0 g, at least 2.0 g, or at least 3.0 g of an anti-CTGF antibody. In some embodiments, the treatment cycle is about 1, 2, 3, 4, 5, 6, 7, 8, 10, 12, or 16 weeks in length. In other embodiments, the treatment cycle comprises 1, 2, 3, 4, 5, 6 or 8 antibody administrations.

In a further aspect of the invention, a method is provided for treating pancreatic cancer in a subject comprising administering to the subject a sufficient quantity of an anti-CTGF antibody to achieve an antibody exposure expressed as the area under the curve 0-14 days ($AUC_{0-14}$) of at least 80,000 μg*h/ml.

In one aspect of the invention, a method is provided for treating pancreatic cancer in a subject comprising administering a sufficient quantity of an anti-CTGF antibody in one treatment cycle to achieve at least 80 μg/ml blood per $m^2$ of patient body surface when the subject's blood is measured at the end of the treatment cycle.

In another aspect, the invention provides a method for treating a CTGF-associated cancer in a subject comprising administering a first dose of an anti-CTGF antibody, wherein the first dose is at least 15 mg/kg. In some embodiments, the first dose is sufficient to achieve an anti-CTGF antibody blood exposure expressed as the area under the curve 0-336 hours ($AUC_{0-336}$) of at least 80,000 μg*h/ml. In other embodiments, the first dose is sufficient to achieve at least 80 μg/ml in blood per $m^2$ of the subject's body surface when the subject's blood is measured at day 14 post-administration of the first dose.

In some embodiments, the method further comprises administering a second dose of the anti-CTGF antibody. In particular embodiments, the first dose and the second dose have same quantity of anti-CTGF antibody, while in other embodiments, the second dose has a higher quantity of anti-CTGF antibody than the first dose. In other embodiments, the second dose has a lower quantity of anti-CTGF antibody than the first dose.

In some embodiments, the method further comprises obtaining a first biologic sample from the subject after the administration of the first antibody dose and measuring a first anti-CTGF antibody concentration. In some embodiments, the first biologic sample is a whole blood, serum or plasma sample. In other embodiments, the first biologic sample is obtained about 7 to about 21 days after administration of the first antibody dose. In further embodiments, the first anti-CTGF antibody concentration is compared to a first target anti-CTGF antibody concentration. In still further embodiments, if the first anti-CTGF antibody concentration is below the first target anti-CTGF body concentration, then the amount of anti-CTGF antibody administered as a second dose is calculated to meet or exceed the first target antibody concentration when a second biologic sample is measured at a substantial similar time point as the first biologic sample. In some embodiments, the first target antibody blood level is at least 50 μg/ml, 75 μg/ml, 100 μg/ml, 125 μg/ml, 150 μg/ml, 200 μg/ml, 250 μg/ml, 300 μg/ml, 400 μg/ml or 500 μg/ml.

In some embodiments, the method further comprises obtaining a second biologic sample from the subject after the administration of the second anti-CTGF antibody dose and measuring a second anti-CTGF antibody concentration. In some embodiments, the second biologic sample is a whole blood, serum or plasma sample. In other embodiments, the second anti-CTGF antibody concentration is measured about 7 to 21 days after administration of the second dose. In further embodiments, the second anti-CTGF antibody concentration is compared to a second target anti-CTGF antibody concentration. In still further embodiments, the second target antibody concentration is at least 50 μg/ml, 75 μg/ml, 100 μg/ml, 125 μg/ml, 150 μg/ml, 200 μg/ml, 250 μg/ml, 300 μg/ml, 400 μg/ml or 500 μg/ml. In other embodiments, the second target antibody blood level is higher than the first target antibody blood level.

In some embodiments, the CTGF-associated cancer is selected from the group consisting of acute lymphoblastic leukemia, angiolipoma, angioleiomyoma, breast carcinoma, colon cancer, fibrosarcoma, gastric cancer, glioma, liver cancer, ovarian cancer, pancreatic cancer, papillary thyroid carcinoma and rhabdomyosarcoma. In particular embodiments, the pancreatic cancer is an adenocarcinoma, while in other embodiments, the pancreatic cancer is a ductal adenocarcinoma. In further embodiments, the CTGF-associated cancer is a desmoplastic cancer. In some embodiments, the subject has a chemotherapy naïve cancer.

In some embodiments, the anti-CTGF antibody is a monoclonal antibody or a fragment thereof that specifically binds to CTGF. In further embodiments, the antibody is the antibody produced by the cell line identified by ATCC Accession No. PTA-6006. In other embodiments the anti-CTGF antibody is CLN1.

In some embodiments, the method further comprises administering to the subject a therapeutically effective amount of a chemotherapy agent. In particular embodiments, the chemotherapy agent is gemcitabine or erlotinib.

In one aspect, a method is provided for treating a CTGF-associated cancer in a subject, the method comprising administering a first dose of an anti-CTGF antibody, wherein the first dose is sufficient to achieve an anti-CTGF antibody blood exposure expressed as the area under the curve 0-336 hours ($AUC_{0-336}$) of at least 80,000 μg*h/ml.

In another aspect, a method is provided for treating a CTGF-associated cancer in a subject, the method comprising administering a first dose of an anti-CTGF antibody, wherein the first dose is sufficient to achieve at least 60 μg/ml in blood per $m^2$ of the subject's body surface when the subject's blood is measured at day 14 post-administration of the first dose.

In a further aspect, a method is provided for treating a CTGF-associated cancer in a subject, the method comprising administering a first dose of an anti-CTGF antibody, wherein the first dose is sufficient to achieve at least 150 μg/ml in blood when the subject's blood is measured at day 14 post-administration of the first dose.

In one aspect of the invention, a method is provided for treating pancreatic cancer in a subject comprising a) administering a first dose of an anti-CTGF antibody; b) measuring a first anti-CTGF antibody blood level in the patient; c) comparing the first anti-CTGF antibody blood level to a first target anti-CTGF antibody blood level and d) administering a second dose of the anti-CTGF antibody calculated to achieve or exceed the first target anti-CTGF antibody blood level when a second measurement of antibody blood level is performed at substantially the same time interval post-administration as the first antibody blood level. By "level" of the anti-CTGF antibody in this context is intended the concentration of anti-CTGF antibody.

In one aspect of the invention, a method is provided for treating pancreatic cancer in a subject comprising administering in one treatment cycle at least 1.0, 1.5, 2.0, 2.5, 3.0, 4.0, 5.0, 6.0, 7.0, 8.0 or 10.0 g of an anti-CTGF antibody. In some embodiments, the treatment cycle is at least 1, 2, 3, 4, 5, 6, 7, 8, 10, 12, or 16 weeks in length. In other embodiments, the treatment cycle comprises at least 1, 2, 3, 4, 5, 6 or 8 antibody administrations.

In another aspect of the invention, a method is provided for extending the time to disease progression (TTP), overall survival (OS) or progression-free survival (PFS) in a subject with a CTGF-associated cancer or desmoplastic cancer, the method comprising administering an effective amount of an anti-CTGF antibody in conjunction with a chemotherapy agent in an amount that extends TTP, OS or PFS in the subject more than TTP, OS, or PFS achieved by administering the chemotherapy agent alone. In some embodiments, the CTGF-associated cancer or desmoplastic cancer is pancreatic cancer. In further embodiments, the method extends TTP by at least 1 month longer than TTP achieved with the chemotherapy agent. In other embodiments, the method extends OS by at least 1 month longer than OS achieved with the chemotherapy agent. In further embodiments, the method extends PFS by at least 1 month longer than PFS achieved with the chemotherapy agent. In further embodiments, the method extends TTP, OS or PFS by at least 1 month beyond that seen with chemotherapy alone without a corresponding increase in the number of occurences or severity of adverse events beyond what is seen with just chemotherapy alone. In certain embodiments, a dose of at least 15 mg/kg of the anti-CTGF antibody is administered. In other embodiments, the chemotherapy agent is gemcitabine.

In one aspect of the invention, an anti-CTGF antibody is provided for use in treating a CTGF-associated cancer in a subject, wherein the subject has a pretreatment CTGF blood level ≤10 ng/ml.

In another aspect of the invention, an anti-CTGF antibody is provided for use in treating a CTGF-associated cancer in a subject, wherein the subject's cancer is advanced.

In a further aspect of the invention, an anti-CTGF antibody is provided for use in treating a CTGF-associated cancer in a subject, wherein the antibody is administered in an amount that results in at least a 50% reduction in the pretreatment blood level of a tumor marker. In some embodiments, the tumor marker is selected from the group consisting of carcinoembryonic antigen (CEA), carbohydrate antigen 19-9 (CA 19-9), UL16 binding protein 2 (ULBP2), carcinoembryonic antigen-related cell adhesion molecule 1 (CEACAM1), MUC1, alpha-fetoprotein, apolipoprotein C-I (ApoC-I), apolipoprotein A-II (ApoA-II), pancreatic associated antigen (Span-1), CA50 antigen, DU-PAN-2, serum amyloid A, insulin-like growth factor-binding protein-1a (IGFBP-1a), M2-pyruvate kinase, alpha4GnT, NPC-1C, elastase-1, tissue polypeptide antigen (TPA) and tissue polypeptide-specific antigen (TPS). In particular embodiments, the tumor marker is CA 19-9.

In a still further aspect of the invention, an anti-CTGF antibody is provided for use in treating a CTGF-associated cancer is a subject, wherein the antibody is for reducing circulating CTGF levels.

In a further aspect of the invention, an anti-CTGF antibody is provided wherein administration of an effective amount of the antibody to a subject results in at least a 10% reduction in a tumor's pretreatment standardized uptake value (SUV) of $^{18}$F-fluorodeoxyglucose ($^{18}$FDG) as measure by positron emission tomography (PET).

In some embodiments, the anti-CTGF antibody is a monoclonal antibody or a fragment thereof that specifically binds to CTGF. In other embodiments, the antibody is produced by the cell line identified by ATCC Accession No. PTA-6006, or a derivative thereof that specifically binds to CTGF. In other embodiments the anti-CTGF antibody is CLN1.

These and other embodiments of the present invention will readily occur to those of skill in the art in light of the disclosure herein, and all such embodiments are specifically contemplated. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DESCRIPTION OF THE INVENTION

Figure 1:
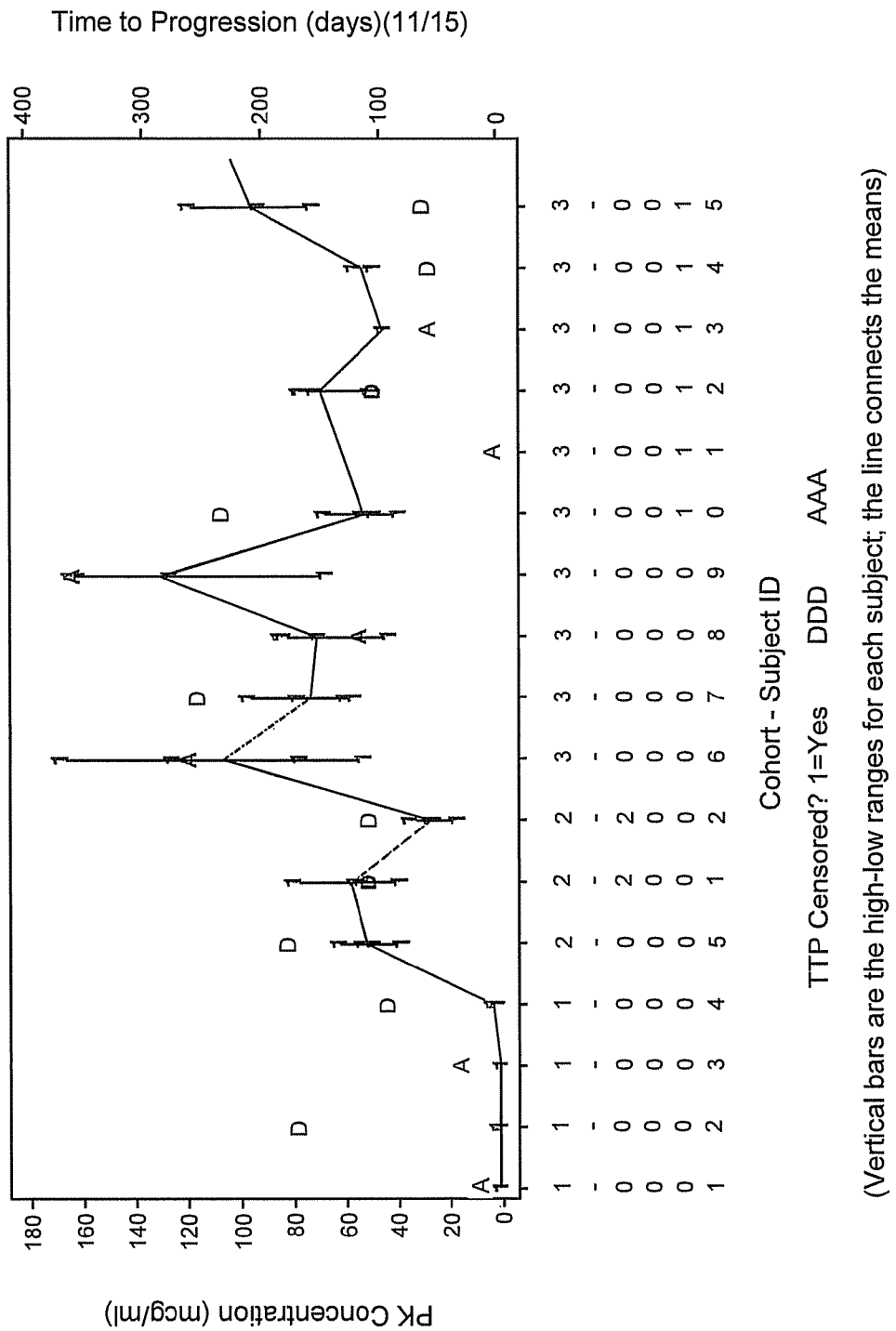
FIG. 1 illustrates the relationship between anti-CTGF antibody $C_{min}$ values and time to progression (TTP) in patients with advanced pancreatic cancer. Patients received 3 mg/kg, 10 mg/kg or 15 mg/kg per treatment cycle that were two weeks in duration. Increased $C_{min}$ values are associated with increased TTP. Patients 0006 and 0009 had the longest TTP of the patients analyzed at this point in the protocol and surprising, patient 0009 is still alive over 24 months from first receiving treatment. The delay in disease progression seen in patients 0006 and 0009 is related to them having both highest individual $C_{min}$ values and highest mean $C_{min}$ values among all patients.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It should be noted that as used herein and in the appended claims, the singular forms "a," "an," and "the" include plural references unless context clearly dictates otherwise. Thus, for example, a reference to "an anti-CTGF antibody" may include a plurality of such antibodies.

As used herein the terms "about" and "substantially similar" refer to ±10%.

As used herein, the term "subject" and "patient" are used interchangeably to refer to an individual. In a preferred embodiment, said subject is a mammal, preferably primate, and more preferably a human being.

As used herein, the terms "treating," "treatment" and "therapy" mean to administer an anti-CTGF antibody to a subject with a CTGF-associated cancer, including subjects with local disease, advanced disease, cancer metastases, occult disease, micrometastases and/or recurrent cancer. The administration of an anti-CTGF antibody to the subject can have the effect of, but is not limited to, abrogating, reducing or inhibiting the growth rate of the CTGF-associated cancer cells; reducing or inhibiting the motility and/or invasiveness of the CTGF-associated cancer cells; abrogating, inhibiting, slowing or reversing the progression rate of the CTGF-associated cancer including stabilizing the disease; increasing time to progression (TTP), increasing progression-free survival (PFS), increasing disease-free survival (DFS), increasing overall survival (OS) or increasing the 1-year survival rate of treated patients, including patients with metastatic and/or recurrent disease. The effect of administration of an anti-CTGF antibody to the subject further includes the reduction or amelioration of at least one clinical symptom afflicting the subject with a CTGF-associated cancer. Additionally, the administration of an anti-CTGF antibody to the subject can elicit the effect of an increase in the patient's Karnofsky performance status, patient's sense of health or wellbeing. In some embodiments, the CTGF-associated cancer is pancreatic cancer. In further embodiments, treatment with an effective amount on an anti-CTGF antibody may reduce, ameliorate or reverse a clinical symptom associated with pancreatic cancer including anorexia, weight loss, fatigue, jaundice, pain, including abdominal pain, analgesic or narcotic consumption, nausea, indigestion, diarrhea, bloating, malaise, itching, dehydration, loss of appetite or hyperglycemia.

As used herein, the term "blood" encompasses whole blood, serum or plasma. When a specific antibody concentration in the blood, e.g., a target antibody blood level, is discussed, it is to be understood to include the antibody concentration in whole blood, serum or plasma.

The terms "first target antibody blood level" and "first target blood level" as used herein refer to the target level of antibody in the blood that is compared to with a measured antibody level. Similarly, the terms "second target antibody blood level" and "second target blood level" refer to the target level of antibody in the blood that is compared with a measured antibody level.

"Connective Tissue Growth Factor (CTGF)" is a 36 kD, cysteine-rich, heparin binding, secreted glycoprotein originally isolated from the culture media of human umbilical vein endothelial cells. (Bradham et al. (1991) *J Cell Biol* 114: 1285-1294; Grotendorst and Bradham, U.S. Pat. No. 5,408, 040.) CTGF belongs to the CCN (TGF, Cyr61, Nov) family of proteins, which includes the serum-induced immediate early gene product Cyr61, the putative oncogene Nov, and the Wnt-inducible secreted proteins (WISP)-1,-2, and -3. (See, e.g., O'Brian et al. (1990) *Mol Cell Biol* 10:3569-3577; Joliot et al. (1992) *Mol Cell Biol* 12:10-21; Ryseck et al. (1991) *Cell Growth and Diff* 2:225-233; Simmons et al. (1989) *Proc. Natl. Acad. Sci. USA* 86:1178-1182; Pennica et al. (1998) *Proc Natl Acad Sci USA*, 95:14717-14722; and Zhang et al. (1998) *Mol Cell Biol* 18:6131-6141.) CCN proteins are characterized by conservation of 38 cysteine residues that constitute over 10% of the total amino acid content and give rise to a modular structure with N- and C-terminal domains. The modular structure of CTGF includes conserved motifs for insulin-like growth factor binding proteins (IGF-BP) and von Willebrand's factor (VWC) in the N-terminal domain, and thrombospondin (TSP1) and a cysteine-knot motif in the C-terminal domain.

CTGF expression is induced by various factors including TGF-β family members, e.g., TGF-β1, activin, etc.; thrombin, vascular endothelial growth factor (VEGF), endothelin and angiotensin II. (Franklin (1997) *Int J Biochem Cell Biol* 29:79-89; Wunderlich (2000) *Graefes Arch Clin Exp Ophthalmol* 238:910-915; Denton and Abraham (2001) *Curr Opin Rheumatol* 13:505-511; and Riewald (2001) *Blood* 97:3109-3116; Xu et al. (2004) *J Biol Chem* 279:23098-23103.) Such factors have been associated with tumorigenesis previously. Therefore, in one aspect, the present invention is directed to treatment of cancers whose negative prognosis is correlated with the expression or activity of these factors, e.g., TGF-β.

Although the present invention demonstrates the role of CTGF in tumor survival, expansion, and metastasis, by demonstrating that agents that target and therefore reduce the concentration of CTGF in a pancreatic cancer patient's body can reduce tumor metabolic activity and increase patient TTP and overall survival, the invention specifically contemplates a similar role for other CCN family members, particularly Cyr61.

CTGF-associated cancers are those cancers characterized by the overexpression of CTGF where elevated CTGF levels are implicated in tumorigenesis, tumor cell proliferation, tumor cell migration and invasion, tumor-associated angiogenesis and/or the formation of desmoplasia. Clinical, in CTGF-associated cancers, the level of CTGF mRNA and/or protein expression is associated with tumor size, clinical stage, presence of metastases and clinical outcome with higher levels associated with worse prognosis. CTGF-associated cancers include acute lymphoblastic leukemia, angiolipoma, angioleiomyoma, breast carcinoma, colon cancer, dermatofibromas, fibrosarcoma, glioma, including glioblastomas, liver cancer, melanoma, pancreatic cancer, papillary thyroid carcinoma and sarcomas, including leiomyosarcoma, chondrosarcoma and rhabdomyosarcoma.

The treatment of desmoplasias and cancers that induce desmoplasias is also contemplated. Desmoplasias comprise a connective tissue capsule that surrounds a tumor and may limit the access of chemotherapy and immunotherapy agents to the tumor. Desmoplasia are frequently seen in pancreatic cancer, ductal breast carcinoma, colon cancer, glioblastomas, sarcomas, including desmoplastic small-round-cell tumor, cutaneous leiomyosarcoma, melanoma, medulloblastoma, and mesothelioma, desmoplastic ganglioglioma, desmoplastic astrocytoma. In pancreatic cancer, desmoplasmias may be induced by tumor CTGF expression and desmoplastic tissue may further express large amounts of CTGF, thus, desmoplasias represent a target for anti-CTGF antibody therapy.

"Pancreatic cancer," "pancreatic tumor" or "tumor", as used herein, includes any tumor located in, derived from, or originating from cells of the pancreas. This includes primary tumors originating in the pancreas, secondary tumors originating in the pancreas or another organ, etc. In one aspect, the present methods and compounds apply to the treatment of pancreatic cancer including, but not limited to, adenocarcinomas of the pancreas and particularly ductal adenocarcinomas of the pancreas. The terms "pancreatic tumor" and "tumor" further includes pancreatic tumor metastases. Pancreatic cancer further includes recurrent or refractory disease. In one aspect, the present methods and compounds apply to the treatment of pancreatic cancer including, but not limited to, adenocarcinomas of the pancreas and particularly ductal adenocarcinomas of the pancreas.

An "advanced" cancer, as used herein, refers to a cancer that has spread outside of the tissue or organ of origin, either by local invasion, lymph node involvement, or by metastasis.

A "refractory" cancer, as used herein, refers to a cancer that has progressed even though an anti-cancer agent, such as a chemotherapy agent, was being administered to the patient. An example of a refractory cancer is one that is refractory to treatment with gemcitabine.

A "recurrent" cancer, as used herein, refers to a cancer that has regrown, either at the initial site or at a distant site, following an initial response to therapy.

As used herein, the terms "time to progression" or "TTP" refer to the time, generally measured in weeks or months, from the time of initial treatment, e.g., with an anti-CTGF antibody such as CLN1, until the cancer progresses. Such a progression can be evaluated by a skilled physician. In the case of pancreatic cancer, progression can be measured by Response Evaluation Criteria in Solid Tumors 1.0 (RECIST 1.0), $^{18}$F-fluorodeoxyglucose ($^{18}$FDG) positron emission tomography (PET) or other suitable means.

The term "extending TTP" refers to an increase in time to disease progression in a treated patient relative to an untreated patient, i.e., relative to a patient not treated with an anti-CTGF antibody.

As used herein, the term "overall survival" (OS) refers to the patient remaining alive for a defined period of time, such as 9 months from the time of initial diagnosis or treatment.

As used herein, the term "progression-free survival" (PFS) refers to the patient remaining alive and without cancer progression.

The term "extending survival" means increasing overall survival or progression-free survival in a treated patient relative to an untreated patient, i.e., relative to a patient not treated with an anti-CTGF antibody.

As used herein, the term "$C_{min}$" is defined as the minimum or trough concentration of an agent, typically in a blood sample, observed in a dosing or treatment cycle, usually measured just prior to the administration of a subsequent dose of the agent.

A "package insert" is used to refer to instructions customarily included in commercial packages of therapeutic products that contain information about the indications, usage, dosage, administration, contraindications, other therapeutic products to be combined with the packaged product, and/or warnings concerning the use of such therapeutic products, etc.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18th ed., Mack Publishing Co.; Hardman, J. G., Limbird, L. E., and Gilman, A. G., eds. (2001) *The Pharmacological Basis of Therapeutics*, 10th ed., McGraw-Hill Co.; Colowick, S. et al., eds., *Methods In Enzymology*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2nd edition, Vols. I-III, Cold Spring Harbor Laboratory Press; Ausubel, F. M. et al., eds. (1999) *Short Protocols in Molecular Biology*, 4th edition, John Wiley & Sons; Ream et al., eds. (1998) *Molecular Biology Techniques: An Intensive Laboratory Course*, Academic Press; Newton, C. R., and Graham, A., eds. (1997) *PCR (Introduction to Biotechniques Series)*, 2nd ed., Springer Verlag.

The section headings are used herein for organizational purposes only, and are not to be construed as in any way limiting the subject matter described herein.

Antibodies

The term "antibody" includes whole antibodies and any antigen binding fragment or a single chain thereof. Thus an antibody includes any protein or peptide-containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework (FR) region, or any portion thereof. Antibody includes intact immunoglobulin molecules as well as to fragments thereof, such as Fab, F(ab')2, and Fv fragments, as well as recombinant, synthetic, and genetically engineered versions thereof, which are capable of binding the epitopic determinant, and include polyclonal and monoclonal antibodies. Anti-CTGF antibodies (i.e., antibodies that bind CTGF or fragments of CTGF) can be prepared using intact CTGF polypeptides or using fragments containing small peptides of interest as the immunizing antigen. The polypeptide or oligopeptide used to immunize an animal (e.g., a mouse, rat, rabbit, chicken, turkey, goat, etc.) can be derived, inter alia, from proteolysis of the CTGF protein, the translation of CTGF mRNA, or synthesized chemically, and can be conjugated to a carrier protein if desired. Commonly used carriers chemically coupled to peptides include, for example, bovine serum albumin, thyroglobulin, and keyhole limpet hemocyanin (KLH). Other methods of selecting antibodies (e.g., phage display) having desired specificities are well known in the art.

The term "antibody" is further intended to encompass antibodies, protease digestion fragments thereof, specified portions and variants thereof, including antibody mimetics or comprising portions of antibodies that mimic the structure and/or function of an antibody or specified fragment or portion thereof, including single chain antibodies and antigen-binding fragments thereof. Examples of antigen-binding fragments of an antibody include, but are not limited to, (i) a Fab fragment, a monovalent fragment consisting of the VL, VII, CL and CII, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426, and Huston et al. (1988) Proc. Natl. Acad Sci. USA 85:5879-

5883). These antibody fragments are obtained using conventional techniques known to those with skill in the art, and the fragments are screened for utility in the same manner as are intact antibodies.

The term "neutralizing antibody" as used herein refers to an antibody, preferably a monoclonal antibody, that is capable of substantially inhibiting or eliminating a biological activity of CTGF. Typically, a neutralizing antibody will inhibit binding of CTGF to a cofactor such as TGFβ, to a CTGF-specific receptor associated with a target cell, or to another biological target.

"Anti-CTGF agent" means any agent, molecule, macromolecule, compound, or composition that inhibits, reduces, or stops the activity, function, production or expression of connective tissue growth factor. The anti-CTGF agent is preferably one that is specific for CTGF and exerts its effect directly and specifically on the CTGF protein or on the CTGF gene or mRNA, rather than a non-specific inhibitor (e.g., a non-specific protease or transcription inhibitor) or an indirect inhibitor (e.g., an inhibitor of an upstream inducer of CTGF). Anti-CTGF agents are well known in the art and are further described herein.

"Anti-CTGF antibody" is an antibody that specifically binds CTGF (i.e, recognizes an epitope of a CTGF polypeptide or fragment). As used herein, "specific binding" refers to antibody binding to a predetermined antigen. Typically, the antibody binds the antigen with a dissociation constant ($K_D$) of $10^{-7}$ M or less, and binds to the predetermined antigen with a $K_D$ that is at least 1.5-fold less (preferably at least 2-fold less, more preferably at least 5-fold less) than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which specifically binds to an antigen". Anti-CTGF antibodies used in the present invention preferably have a $K_D$ for CTGF of $10^{-8}$ M or less.

In some embodiments, the anti-CTGF antibody is CLN-1 described in U.S. Pat. No. 7,405,274, that is incorporated by reference herein in its entirety or an antibody that binds to the same epitope as CLN-1.

A "naked antibody" for the purposes herein is an antibody that is not conjugated to a cytotoxic moiety or radiolabel. In some embodiments, the anti-CTGF antibody is a naked antibody.

Exemplary antibodies for use in the methods of the present invention are described, e.g., in U.S. Pat. No. 5,408,040; PCT/US1998/016423; PCT/US1999/029652 and International Publication No. WO 99/33878. Preferably, the anti-CTGF antibody for use in the method is a monoclonal antibody.

Preferably the antibody is a neutralizing antibody. In particular embodiments, the antibody is an antibody described and claimed in U.S. Pat. Nos. 7,405,274 and 7,871,617. In some embodiments, the antibody has the amino acid sequence of the antibody produced by the cell line identified by ATCC Accession No. PTA-6006. In other embodiments, the antibody binds to CTGF competitively with an antibody produced by the cell line identified by ATCC Accession No. PTA-6006. In further embodiments, the antibody binds to the same epitope as the antibody produced by ATCC Accession No. PTA-6006. A particular antibody for use in the present methods is CLN1 or mAb1, as described in U.S. Pat. No. 7,405,274 and U.S. patent application Ser. No. 12/148,922, or an antibody substantially equivalent thereto or derived therefrom.

As used herein, "specific binding" refers to antibody binding to a predetermined antigen. Typically, the antibody binds the antigen with a dissociation constant ($K_D$) of $10^{-7}$ M or less, and binds to the predetermined antigen with a $K_D$ that is at least 1.5-fold less (preferably at least 2-fold less, more preferably at least 5-fold less) than its $K_D$ for binding to a non-specific antigen (e.g., bovine serum albumin or casein) other than the predetermined antigen or a closely-related antigen. The phrases "an antibody recognizing an antigen" and "an antibody specific for an antigen" are used interchangeably herein with the term "an antibody which specifically binds to an antigen".

As referred to herein, the phrase "an antibody that specifically binds to CTGF" includes any antibody that binds to CTGF with high affinity. Affinity can be calculated from the following equation:

$$\text{Affinity} = K_a = \frac{[Ab \cdot Ag]}{[Ab][Ag]} = \frac{1}{K_d}$$

where [Ab] is the concentration of the free antigen binding site on the antibody, [Ag] is the concentration of the free antigen, [Ab·Ag] is the concentration of occupied antigen binding sites, Ka is the association constant of the complex of antigen with antigen binding site, and Kd is the dissociation constant of the complex. A high-affinity antibody typically has an affinity at least on the order of $10^8 M^{-1}$, $10^9 M^{-1}$ or $10^{10} M^{-1}$. In particular embodiments, an antibody for use in the present methods will have a binding affinity for CTGF between of $10^8 M^{-1}$ and $10^{10} M^{-1}$, between $10^8 M^{-1}$ and $10^9 M^{-1}$ or between $10^9 M^{-1}$ and $10^1 M^{-1}$. In some embodiments, the high-affinity antibody has an affinity of about $10^8 M^{-1}$, $10^9 M^{-1}$ or $10^1 M^{-1}$. Anti-CTGF antibodies used in the present invention preferably have a $K_D$ for CTGF of $10^{-8}$ M or less.

Antibody Mimetics

Antibody mimetics are proteins, typically in the range of 3-25 kD that are designed to bind an antigen with high specificity and affinity like an antibody, but are structurally unrelated to antibodies. Frequently, antibody mimetics are based on a structural motif or scaffold that can be found as a single or repeated domain from a larger biomolecule. Examples of domain derived antibody mimetics included AdNectins that utilize the 10th fibronectin III domain (Lipovgêk D. *Protein Eng Des Sel,* 2010, 24:3-9); Affibodies that utilize the Z domain of *staphylococcal* protein A (Nord K et al. *Nat Biotechnol.* 1997, 15: 772-777) and DARPins that utilize the consensus ankyrin repeat domain (Amstutz P. *Protein Eng Des Sel.* 2006, 19:219-229. Alternatively, antibody mimetics can also be based on the entire structure of a smaller biomolecule, such as Anticalins that utilize the lipocalin structure (Beste G et al. *Proc Natl Acad Sci USA.* 1999, 5:1898-1903)

Methods

The present invention provides methods useful for treating CTGF-associated cancers or desmoplastic cancers including pancreatic cancer. In one aspect of the invention, a method is provide for treating pancreatic cancer in a subject, the method comprising administering a sufficient quantity of an anti-CTGF antibody to the subject in a treatment cycle to achieve a $C_{min}$ antibody concentration in blood per square meter of body surface area of at least 40 µg/ml/m², 50 µg/ml/m², 60 µg/ml/m², 70 µg/ml/m², 80 µg/ml/m², 90 µg/ml/m² or 100 µg/ml/m². In a preferred embodiment, a sufficient quantity of an anti-CTGF antibody is administered to the subject to achieve a $C_{min}$/m² of at least 50 µg/ml/m² after the first treatment cycle. In another preferred embodiment, a sufficient quantity of an anti-CTGF antibody is administered to the subject in each of two treatment cycles to achieve a $C_{min}/m^2$ of at least 60 µg/ml/m² after the second treatment cycles. In a further preferred embodiment, a sufficient quantity of an anti-CTGF antibody is administered to the subject in each of three treatment cycles to achieve a $C_{min}/m^2$ of at least 70 µg/ml/m² after the third treatment cycle. In another preferred embodiment, a sufficient quantity of an anti-CTGF antibody is administered to the subject in each of four treatment cycles to achieve a $C_{min}/m^2$ of at least 80 µg/ml/m² after the fourth treatment cycle. In further embodiments, a sufficient quantity of an anti-CTGF antibody is administered to the subject in each successive treatment cycle to achieve a mean $C_{min}/m^2$ of at least 50 µg/ml/m², 60 µg/ml/m², 70 µg/ml/m², 80 µg/ml/m², 90 µg/ml/m², 100 µg/ml/m² or 120 µg/ml/m². In particular embodiments, the mean $C_{min}/m^2$ is at least 50 µg/ml/m². In other embodiments, the mean $C_{min}/m^2$ is in a range of 50 µg/ml/m²-80 µg/ml/m², 80 µg/ml/m²-100 µg/ml/m² or 100 µg/ml/m²-120 µg/ml/m².

In one embodiment, the quantity of anti-CTGF antibody that is sufficient to achieve a $C_{min}/m^2$ after one treatment cycle of at least 50 µg/ml/m² is at least 1.0 g. In another embodiment, the quantity of antibody that is sufficient to achieve a $C_{min}/m^2$ after one treatment cycle of at least 50 µg/ml/m² is the total amount of antibody calculated by multiplying a subject's body weight (in kg) by 15 mg/kg.

In a further aspect, a method is provided to treat pancreatic cancer in a subject, the method comprising the administration of an anti-CTGF antibody dose that is sufficient to achieve an antibody $C_{min}$ in blood of at least 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml or 200 µg/ml. In some embodiments, the $C_{min}$ is measured for a treatment cycle of about 2, 3, 4, 5, 6, 7, 8, 9, 10, 11, 12, 13, 14, 15, 16, 17, 18, 19, 20, 21, 22, 23, 24, or 28 days. In a preferred embodiment, the antibody dose is sufficient to achieve a $C_{min}$ of at least 50 µg/ml for a treatment cycle of about 14 days. In another preferred embodiment, a sufficient quantity of an anti-CTGF antibody is administered to the subject to achieve a $C_{min}$ after one treatment cycle of at least 60 µg/ml. In a further preferred embodiment, a sufficient quantity of an anti-CTGF antibody is administered to the subject in each of two treatment cycles to achieve a $C_{min}$ after two treatment cycles of at least 70 µg/ml. In a still further preferred embodiment, a sufficient quantity of an anti-CTGF antibody is administered to the subject in each of three treatment cycles to achieve a $C_{min}$ after the third three treatment cycle of at least 80 µg/ml. In another preferred embodiment, a sufficient quantity of an anti-CTGF antibody is administered to the subject in each of four treatment cycles to achieve a $C_{min}$ after the fourth treatment cycle of at least 90 µg/ml. In one embodiment, the quantity of anti-CTGF antibody that is sufficient to achieve a $C_{min}$ of at least 50 µg/ml after one treatment cycle is at least 1.0 g.

In another aspect of the invention, a method is provided to treat pancreatic cancer in a subject, the method comprising the administration of a sufficient quantity of an anti-CTGF antibody to achieve an antibody exposure in blood expressed as the area under the curve (AUC) of at least 60,000 µg*h/ml, 80,000 µg*h/ml, 100,000 µg*h/ml, 120,000 µg*h/ml, or 140,000 µg*h/ml. In some embodiments, the AUC is calculated from about 0-4 days, 0-5 days, 0-6 days, 0-7 days, 0-8 days, 0-9 days, 0-10 days, 0-11 days, 0-12 days, 0-13 days, 0-14 days, 0-16 days, 0-18 days 0-21 days, or 0-28 days. In some preferred embodiments, the time period is from 0-14 days (0-336 hours) following antibody administration. In one embodiment, the quantity of anti-CTGF antibody that is sufficient to achieve an $AUC_{0-336\ hours}$ of at least 80,000 µg*h/ml after one treatment cycle is at least 1.0 g.

In a further aspect of the invention, a method is provided for treating pancreatic cancer in a subject, the method comprising administering an anti-CTGF antibody dose of at least 1.0 g. In some embodiments, the anti-CTGF antibody dose is at least 1.0 g, 1.5 g, 2.0 g, 2.5 g, 3.0 g, 3.5 g, 4.0 g, 5.0 g, 6.0 g, 8.0 g or 10.0 g of anti-CTGF antibody. In other embodiments, the antibody dose is not more than 1.0 g, 1.5 g, 2.0 g, 2.5 g, 3.0 g, 3.5 g, 4.0 g, 5.0 g, 6.0 g, 8.0 g or 10.0 g of an anti-CTGF antibody. In further embodiments, the antibody dose is in the range of about 0.5 g-1.0 g, 1.0-2.0 g, 2.0-3.0 g, 3.0-4.0 g, 4.0-5.0 g, 5.0-6.0 g, 6.0-8.0 g or 8.0-10.0 g. In preferred embodiments, the antibody dose is about 1.05 g, 1.25 g, 1.60 g, 1.75 g, 2.0 g, 2.50 g, 3.15 g or 3.85 g for a standard 70 kg man; the dose can be adjusted accordingly for patients of other weights.

In a still further aspect of the invention, a method is provided for treating pancreatic cancer in a subject, the method comprising administering an anti-CTGF antibody dose of at least 15 mg/kg. In some embodiments, the anti-CTGF antibody dose is at least 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In other embodiments, the antibody dose is not more than 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In further embodiments, the antibody dose is between 15 mg/kg-55 mg/kg, 15 mg/kg-20 mg/kg, 20 mg/kg-25 mg/kg, 25 mg/kg-35 mg/kg, 35 mg/kg-45 mg/kg, 45 mg/kg-55 mg/kg. In preferred embodiments, the antibody dose is about 15 mg/kg, 17.5 mg/kg, 20 mg/kg, 22.5 mg/kg, 25 mg/kg, 35 mg/kg, 45 mg/kg or 55 mg/kg In another aspect of the invention, a method is provide for treating pancreatic cancer in a subject, the method comprising administering at least 500 mg/m² of an anti-CTGF antibody. In some embodiments, the anti-CTGF antibody dose is at least 500 mg/m², 600 mg/m², 700 mg/m², 800 mg/m², 900 mg/m², 1,000 mg/m² 1,200 mg/m², 1,400 mg/m², 1,600 mg/m², 1,800 mg/m², 2,000 mg/m² or 2,200 mg/m². In other embodiments, the antibody dose of not more than about 700 mg/m², 800 mg/m², 900 mg/m², 1,000 mg/m², 1,200 mg/m², 1,400 mg/m², 1,600 mg/m², 1,800 mg/m², 2,000 mg/m² or 2,200 mg/m². In further embodiments, the antibody dose is in a range from about 600 mg/m²-800 mg/m², 800 mg/m²-1,200 mg/m², 1,200 mg/m²-1,600 mg/m² or 1,600 mg/m²-2,200 mg/m². In preferred embodiments, the antibody dose is about 550 mg/m², 600 mg/m², 700 mg/m², 1,000 mg/m², 1,400 mg/m², 1,800 mg/m² or 2,200 mg/m².

In a further aspect of the invention, a method is provided for treating pancreatic cancer in a subject, the method comprising administering an effective amount of an anti-CTGF antibody to reduce the blood level of CTGF by at least 10%, 20%, 30%, 40%, 50%, 60%, 70%, 80%, 90% or 95% compared to a baseline CTGF blood level obtained prior to anti-CTGF antibody treatment. In some embodiments, the blood level of CTGF is reduced to a concentration of less than 20 ng/ml, 15 ng/ml, 10 ng/ml, 5 ng/ml, 1 ng/ml or 0.1 ng/ml. In a preferred embodiment, for the treatment of pancreatic cancer, treatment with an anti-CTGF antibody reduces CTGF blood level to <10 ng/ml. In particular embodiments, the CTGF blood level includes the contribution of CTGF fragments such as an N-terminal fragment.

In one aspect, methods are provided for administering an anti-CTGF antibody based on titrating the antibody level in a patient's blood (whole blood, plasma or serum) or other biologic sample. The term "titrating" encompasses the idea that a threshold antibody level in a patient is beneficial or necessary in order to improve the current medical condition or prognosis of a cancer patient. Using blood as an exemplary biological sample, titrating entails treating a patient with a set first antibody dose based on the patient's age, gender, performance status, concurrent medical conditions, tumor burden and other similar factors. Then after a specific time point, a first blood sample is obtained from the patient and assayed for antibody level to determine a first blood level of the antibody. In some embodiments, the blood sample (biological sample) is obtained about 2, 3, 4, 5, 6, 7, 8, 9, 10, 11, 12, 13, 14, 15, 16, 17, 18, 19, 20, 21, 24 or 28 days post-administration.

Next, the first blood level of anti-CTGF antibody is compared to a first target blood level of anti-CTGF antibody. This first target antibody blood level is chosen based on the analysis of past patient data where patients below the first target blood level had worse clinical outcomes compared to those patients that had higher antibody levels in their blood. Worse clinical outcomes include shorter time to disease progression, shorter disease free interval or shorter survival compared to patients that have an antibody level at or above the first target level.

If the first blood level of anti-CTGF antibody is at least as high as the first target anti-CTGF antibody blood level, than the healthcare provider will administer a second anti-CTGF antibody dose that is substantially similar to the first antibody dose. If on the other hand, the patient's first blood level of anti-CTGF antibody is lower than a first target anti-CTGF antibody blood level, the healthcare provider will administer a second anti-CTGF antibody dose that is higher than the first anti-CTGF antibody dose in order to compensate for the increased depletion and shorter half-life and hence, lower blood anti-CTGF antibody concentration seen with this patient.

Following the administration of the second anti-CTGF antibody dose calculated to achieve or exceed the first target anti-CTGF antibody blood level, a second blood sample is drawn and assayed for a second anti-CTGF antibody blood level. This second antibody blood level is compared to a second target antibody blood level. If the patient's second antibody blood level is at least as high as the second target antibody blood level, then the next (third) administration will be of a substantially similar concentration of antibody compared to the second administered dose. If the second blood level of antibody is below the second target antibody blood level, the healthcare provider will increase the amount of antibody in the third dose to compensate for the shorter antibody half-life and to ensure that the third dose will achieve or exceed the second target blood level.

The titration process can be continued in a similar manner for as long as necessary or as desired by the healthcare provider. In some instances, the number of titration cycles is at least 2, 3, 4, 5, 6, 7, 8, 10, 12, 16, or 24 cycles. In some embodiments, the target antibody blood level remains the same for each subsequent titration cycle, while in other embodiments, the target antibody blood level increases. In some instances, the increase in the target level is linear, in other exponential and in still others, a staircase increase is used. For example, a first target antibody blood level may be set at about 80 µg/ml, a second target antibody blood level at 100 µg/ml, a third target antibody blood level at 120 µg/ml and so forth, in a linear manner. In another example, a first target antibody blood level may be set at 25 $\mu g/ml/m^2$, a second target antibody blood level of 25 $\mu g/ml/m^2$, a third target antibody blood level of 40 $\mu g/ml/m^2$, a forth target antibody blood level of 40 $\mu g/ml/m^2$, a fifth target antibody blood level of 60 $\mu g/ml/m^2$, a sixth target antibody blood level of 60 $\mu g/ml/m^2$ and so forth in a staircase manner.

Titration accounts for the patient specific differences in various factors such as quantity of antigen, access to antigen, tumor burden, rate of antibody catabolism, rate of antibody excretion and antibody half-life. Patient biological samples can have lower than expected antibody levels based on the level of accessible or free antigen (CTGF) in blood, normal tissue, tumor and tumor stroma. A large quantity of available antigen can bind to and therefore, reduce the amount of antibody that will be detected in a biologic sample. Typically, the biological sample is a blood sample, but other biologic samples are contemplated such as serous fluids from the peritoneal cavity, lungs, or heart; or central nervous system fluid; or a tissue or tumor biopsy or other surgical sample. The antibody level in a patient sample can also be below a target level because of increased catabolism and/or excretion of the antibody compared to other patients.

In patients with a low anti-CTGF antibody level in the blood sample, it is therapeutically beneficial to increase the level of available antibody in the patient. Usually, this means increasing the level or concentration of circulating anti-CTGF antibody found in the patient's blood to that of a target level. In some embodiments, the target blood level is at least about 10 µg/ml, 20 µg/ml, 30 µg/ml, 40 µg/ml, 50 µg/ml, 60 µg/ml, 70 µg/ml, 75 µg/ml, 80 µg/ml, 90 µg/ml, 100 µg/ml, 110 µg/ml, 125 µg/ml, 150 µg/ml or 200 µg/ml. In other embodiments, the target level can be expressed as the antibody concentration $(\mu g/ml)/m^2$, wherein the antibody concentration in the patient's blood sample is divided by the patient's body surface area. This calculation normalizes for difference in patient size. In some embodiments, the target blood level is at least 10 $\mu g/ml/m^2$, 20 $\mu g/ml/m^2$, 25 $\mu g/ml/m^2$, 30 $\mu g/ml/m^2$, 40 $\mu g/ml/m^2$, 50 $\mu g/ml/m^2$, 60 $\mu g/ml/m^2$, 75 $\mu g/ml/m^2$, 80 $\mu g/ml/m^2$, or 100 $\mu g/ml/m^2$.

In some embodiments, a desired target anti-CTGF antibody blood level can be achieved using an antibody dose of at least 400 $mg/m^2$, 500 $mg/m^2$, 600 $mg/m^2$, 700 $mg/m^2$, 800 $mg/m^2$, 900 $mg/m^2$ or 1,000 $mg/m^2$. In other embodiments, a desired target blood level can be achieved using an antibody dose of at least 15 mg/kg, 20 mg/kg, 25 mg/kg, 30 mg/kg, 40 mg/kg, 50 mg/kg, or 100 mg/kg.

In further embodiments, the antibody dose can be titrated based on functional or metabolic imaging of the tumor and any metastatic lesions. Functional imaging includes analysis of blood flow as obtained by magnetic resonance imaging or ultrasound imaging. Metabolic imaging includes analysis of metabolic activity as evidenced by the cellular uptake of a labeled substrate. In one embodiment, the metabolic imaging modality is PET imaging using $^{18}$F-deoxyglucose (FDG). Tumor cells typically uptake FGD at a higher rate than normal cells and therefore generate a bright image that can be distinguished from normal tissue. Treatment with an appropriate antibody concentration can cause tumor cell death resulting in reduced tumor image signal strength. A patient can be titrated using the antibody alone or in combination with other agents using the tumor PET image to guide the dose selection of antibody and other agents. If no decrease is seen in the tumor image signal strength following a first administration, the dose of antibody and/or other agents can be increased in a subsequent treatment with the subject reimaged if desired.

In some embodiments, a patient is treated using an antibody dose that will result in a desired or targeted blood antibody exposure. Typically, blood antibody exposure is expressed as µg*h/ml and the exposure can be calculated from the area under the curve (AUC) for a particular time period. In some embodiments, the AUC is calculated from about 0-8 hrs, 0-12 hrs, 0-14 hrs, 0-16 hrs, 0-24 hrs, 0-30 hrs, 0-36 hrs, 0-48 hrs, 0-64 hrs, 0-72 hrs, 0-96 hrs, 0-120 hrs, 0-144 hrs, 0-288 hrs, 0-336 hrs. In some embodiments the time period is from 0-14 days following antibody administration and the target blood antibody exposure is at least 60,000 μg*h/ml, 80,000 μg*h/ml, 100,000 μg*h/ml, 120,000 μg*h/ml, or 140,000 μg*h/ml.

In some embodiments, the antibody treatment cycle, including titration cycle, may be combined with a treatment cycle of at least one additional therapeutic agent to form a combined treatment cycle. Typically, the antibody and agents will each have a preferred treatment administration schedule. The administration of the antibody and at least one other agent can be simultaneously, or they can be sequential. The administration of one or more antibody therapy/titration cycles with at least one other therapeutic agent therapy cycle can be about 1, 2, 3, 4, 5, 6, 7, 8, 9, 10, 11, 12, or 16 weeks in duration and can be repeated as desired. Typically, a period of time is provided between treatment cycles to allow a patient to recover from the effects of the therapy.

In one aspect, the treatment or titration method exposes the patient in one treatment or titration cycle to a total quantity of anti-CTGF antibody of at least 0.5 g, 1.0 g, 1.5 g, 2.0 g, 2.5 g, 3.0 g, 3.5 g, 4.0 g, 5.0 g, 6.0 g, 8.0 g or 10.0 g. In some embodiments, this treatment or titration cycle is about 1, 2, 3, 4, 5, 6, 7, 8, 10, 12, or 16 weeks in length. In other embodiments, this treatment or titration cycle comprises 1, 2, 3, 4, 5, 6 or 8 antibody administrations.

In some embodiments, the additional therapeutic agent is a chemotherapy agent or immunotherapy agent. In further embodiments, the chemotherapy agent is gemcitabine or erlotinib.

The methods of the present invention are applicable to all patients, particularly human patients, that have CTGF-associated tumors. Patients include those with localized tumors, tumors that have invaded into surrounding tissue and also tumor metastases. With respect to pancreatic cancer, the disclosed anti-CTGF therapy is applicable to all stages of the disease from Stage I-Stage IVB and including cancer recurrences. Anti-CTGF antibodies can be administered using the disclosed methodologies as front-line therapy, in combination with agents that represent the current standard of care, as a neoadjuvant therapy administered before another therapy, such as before surgery. Furthermore, the disclosed methodologies can be administered as maintenance therapy following the successful eradication of the disease.

In one aspect of the invention, a method for treating a CTGF-associated cancer in a subject is provided, the method comprising administering a first dose of an anti-CTGF antibody. In some embodiments, the first anti-CTGF antibody dose is at least 0.5 mg/kg, 1.0 mg/kg, 2.0 mg/kg, 3.0 mg/kg, 4.0 mg/kg, 5.0, mg/kg, 6.0 mg/kg, 7.0 mg/kg, 8.0 mg/kg, 9.0 mg/kg, 10 mg/kg, 12.5 mg/kg, 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In other embodiments, the first antibody dose is not more than about 0.5 mg/kg, 1.0 mg/kg, 2.0 mg/kg, 3.0 mg/kg, 4.0 mg/kg, 5.0, mg/kg, 6.0 mg/kg, 7.0 mg/kg, 8.0 mg/kg, 9.0 mg/kg, 10 mg/kg, 12.5 mg/kg, 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In further embodiments, the first antibody dose is between 0.5 mg/kg-5.0 mg/kg, 5.0 mg/kg-10 mg/kg, 10 mg/kg-15 mg/kg, 15 mg/kg-30 mg/kg, 15 mg/kg-45 mg/kg, 30 mg/kg-45 mg/kg, 45 mg/kg-60 mg/kg, 60 mg/kg-75 mg/kg, 75 mg/kg-100 mg/kg. In preferred embodiments, for the treatment of pancreatic cancer, the first dose is about 15 mg/kg, 17.5 mg/kg, 20 mg/kg, 22.5 mg/kg, 25 mg/kg, 35 mg/kg, 45 mg/kg or 55 mg/kg.

In some embodiments, the first anti-CTGF antibody dose is at least 10 mg/m$^2$, 50 mg/m$^2$, 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1,000 mg/m$^2$, 1,200 mg/m$^2$, 1,400 mg/m$^2$, 1,600 mg/m$^2$, 1,800 mg/m$^2$, 2,000 mg/m$^2$ or 2,200 mg/m$^2$. In other embodiments, the first antibody dose of not more than about 10 mg/m$^2$, 50 mg/m$^2$, 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1,000 mg/m$^2$, 1,200 mg/m$^2$, 1,400 mg/m$^2$, 1,600 mg/m$^2$, 1,800 mg/m$^2$, 2,000 mg/m$^2$ or 2,200 mg/m$^2$. In further embodiments, the first antibody dose is in a range from about 10 mg/m$^2$-100 mg/m$^2$, 100 mg/m$^2$-200 mg/m$^2$, 200 mg/m$^2$-400 mg/m$^2$, 400 mg/m$^2$-800 mg/m$^2$, 800 mg/m$^2$-1,200 mg/m$^2$, 1,200 mg/m$^2$-1,600 mg/m$^2$ or 1,600 mg/m$^2$-2,200 mg/m$^2$. In preferred embodiments, for the treatment of pancreatic cancer, the first dose is about 550 mg/m$^2$, 600 mg/m$^2$, 700 mg/m$^2$, 1,000 mg/m$^2$, 1,400 mg/m$^2$, 1,800 mg/m$^2$ or 2,200 mg/m$^2$.

Alternately, the first anti-CTGF antibody dose may be calculated based on specific patient characteristics such as the patient's age, gender, performance status, concurrent medical conditions, hepatic and renal sufficiency, tumor burden and other factors. In some embodiments, the first anti-CTGF antibody dose is calculated based on a standard antibody dose (mg/kg or mg/m$^2$) that is then "personalized" to account for patient-specific characteristics. For example, if the standard antibody dose is about 15 mg/kg, but the patient has extensive tumor burden that can be expected to act as an antigen sink, thereby reducing the level of circulating antibody in the blood, the antibody dose can be increased, for instance, to about 20 mg/kg, to compensate for the expected reduction in circulating antibody when measured at a particular point in time post-administration.

In other embodiments, the first anti-CTGF antibody dose is an antibody dose that is sufficient to achieve an antibody concentration in blood of at least 0.5 μg/ml, 1 μg/ml, 5 μg/ml, 10 μg/ml, 15 μg/ml, 20 μg/ml, 25 μg/ml, 50 μg/ml, 60 μg/ml, 75 μg/ml, 80 μg/ml, 100 μg/ml, 125 μg/ml, 150 μg/ml, 200 μg/ml, 300 μg/ml or 400 μg/ml, when measured about 2, 3, 4, 5, 6, 7, 8, 9, 10, 11, 12, 13, 14, 15, 16, 17, 18, 19, 20, 21, 22, 23, 24, or 28 days post-administration. In further embodiments, the first antibody dose is sufficient to achieve an antibody concentration in blood in the range of about 0.5 μg/ml-10 μg/ml, 10 μg/ml-20 μg/ml, 20 μg/ml-40 μg/ml, 40 μg/ml-60 μg/ml, 60 μg/ml-100 μg/ml, 100 μg/ml-150 μg/ml, 150 μg/ml-200 μg/ml or 200 μg/ml-400 μg/ml when measured about 2, 3, 4, 5, 6, 7, 8, 9, 10, 11, 12, 13, 14, 15, 16, 17, 18, 19, 20, 21, 22, 23, 24, or 28 days post-administration. In preferred embodiments, for the treatment of pancreatic cancer, the first antibody dose is sufficient to achieve at least 60 μg/ml, 80 μg/ml, 100 μg/ml, 125 μg/ml or 150 μg/ml in blood when measured about 14 days post-administration. In another preferred embodiment, for the treatment of pancreatic cancer, a first antibody dose equal to or greater than 15 mg/kg is administered to achieve at least 100 μg/ml, 125 μg/ml or 150 μg/ml in blood.

In further embodiments, the first anti-CTGF antibody dose is an antibody dose that is sufficient to achieve an antibody $C_{min}$ in blood of at least 0.5 μg/ml, 1 μg/ml, 5 μg/ml, 10 μg/ml, 15 μg/ml, 20 μg/ml, 25 μg/ml, 50 μg/ml, 75 μg/ml, 100 μg/ml, 125 μg/ml, 150 μg/ml or 200 μg/ml when measured during a treatment cycle of about 2, 3, 4, 5, 6, 7, 8, 9, 10, 11, 12, 13, 14, 15, 16, 17, 18, 19, 20, 21, 22, 23, 24, or 28 days in duration. In preferred embodiments, for the treatment of pancreatic cancer, the first antibody dose is sufficient to achieve a $C_{min}$ of at least 100 µg/ml, 125 µg/ml or 150 µg/ml for a treatment cycle of about 14 days.

In further embodiments, the first anti-CTGF antibody dose is sufficient to achieve an antibody concentration in blood of at least 0.5 µg/ml/m$^2$, 1 µg/ml/m$^2$, 10 µg/ml/m$^2$, 15 µg/ml/m$^2$, 20 µg/ml/m$^2$, 25 µg/ml/m$^2$, 30 µg/ml/m$^2$, 40 µg/ml/m$^2$, 45 µg/ml/m$^2$, 50 µg/ml/m$^2$, 60 µg/ml/m$^2$, 75 µg/ml/m$^2$, 80 µg/ml/m$^2$, 100 µg/ml/m$^2$ or 150 µg/ml/m$^2$, when measured about 2, 3, 4, 5, 6, 7, 8, 9, 10, 11, 12, 13, 14, 15, 16, 17, 18, 19, 20, 21, 22, 23, 24, or 28 days post-administration. In other embodiments, the first anti-CTGF antibody dose is sufficient to achieve an antibody concentration in blood of not more than about 0.5 µg/ml/m$^2$, 1 µg/ml/m$^2$, 10 µg/ml/m$^2$, 15 µg/ml/m$^2$, 20 µg/ml/m$^2$, 25 µg/ml/m$^2$, 30 µg/ml/m$^2$, 40 µg/ml/m$^2$, 45 µg/ml/m$^2$, 50 µg/ml/m$^2$, 60 µg/ml/m$^2$, 75 µg/ml/m$^2$, 80 µg/ml/m$^2$, 100 µg/ml/m$^2$ or 150 µg/ml/m$^2$, when measured about 2, 3, 4, 5, 6, 7, 8, 9, 10, 11, 12, 13, 14, 15, 16, 17, 18, 19, 20, 21, 22, 23, 24, or 28 days post-administration. In some embodiments, the first antibody dose is sufficient to achieve an antibody concentration in the range of about 0.5 µg/ml/m$^2$-10 µg/ml/m$^2$, 10 µg/ml/m$^2$-20 µg/ml/m$^2$, 20 µg/ml/m$^2$-40 µg/ml/m$^2$, 40 µg/ml/m$^2$-60 µg/ml/m$^2$, 60 µg/ml/m$^2$-75 µg/ml/m$^2$, 75 µg/ml/m$^2$-100 µg/ml/m$^2$ or 100 µg/ml/m$^2$-150 µg/ml/m$^2$ when measured about 2, 3, 4, 5, 6, 7, 8, 9, 10, 11, 12, 13, 14, 15, 16, 17, 18, 19, 20, 21, 22, 23, 24, or 28 days post-administration. In preferred embodiments, for the treatment of pancreatic cancer, the first antibody dose is sufficient to achieve an antibody concentration of at least 50 µg/ml/m$^2$, 60 µg/ml/m$^2$, 70 µg/ml/m$^2$, 80 µg/ml/m$^2$ or 100 µg/ml/m$^2$ when measured 14 days post-administration.

In further embodiments, the first anti-CTGF antibody dose is sufficient to achieve an antibody exposure of at least 1,000 µg*h/ml, 5,000 µg*h/ml, 10,000 µg*h/ml, 20,000 µg*h/ml, 40,000 µg*h/ml, 60,000 µg*h/ml, 80,000 µg*h/ml, 100,000 µg*h/ml, 120,000 µg*h/ml, or 140,000 µg*h/ml. Typically, blood antibody exposure is calculated from the area under the curve (AUC) for a particular time period. In some embodiments, the AUC is calculated from about 0-4 days, 0-5 days, 0-6 days, 0-7 days, 0-8 days, 0-9 days, 0-10 days, 0-11 days, 0-12 days, 0-13 days, 0-14 days, 0-16 days, 0-18 days 0-21 days, or 0-28 days. In particular embodiments, for the treatment of pancreatic cancer, the time period is from 0-14 days (0-336 hours) following a first antibody administration and the first antibody dose contains sufficient antibody to produce an antibody exposure of at least 60,000 µg*h/ml, 80,000 µg*h/ml, 100,000 µg*h/ml, 120,000 µg*h/ml, or 140,000 µg*h/ml.

In still further embodiments, following the administration of the first anti-CTGF antibody dose, a second dose of anti-CTGF antibody is administered. In some embodiments, the quantity of antibody administered in the second antibody dose is the same quantity administered in the first antibody dose, while in other embodiments, the quantity of antibody administered in the second antibody dose is lesser or greater than the quantity administered in the first antibody dose. In some embodiments, the second antibody dose is at least 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10 mg/kg, 12.5 mg/kg, 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In other embodiments, the second antibody dose is not more than about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10 mg/kg, 12.5 mg/kg, 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In further embodiments, the second antibody dose is between 0.5 mg/kg-5 mg/kg, 5 mg/kg-10 mg/kg, 10 mg/kg-15 mg/kg, 15 mg/kg-30 mg/kg, 30 mg/kg-45 mg/kg, 45 mg/kg-60 mg/kg, 60 mg/kg-75 mg/kg, 75 mg/kg-100 mg/kg. In preferred embodiments, for the treatment of pancreatic cancer, the second dose is about 15 mg/kg, about 17.5 mg/kg, 22.5 mg/kg, about 25 mg/kg, 35 mg/kg, 45 mg/kg or 55 mg/kg.

In some embodiments, the second anti-CTGF antibody dose is at least 10 mg/m$^2$, 50 mg/m$^2$, 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1,000 mg/m$^2$, 1,200 mg/m$^2$, 1,400 mg/m$^2$, 1,600 mg/m$^2$, 1,800 mg/m$^2$, 2,000 mg/m$^2$ or 2,200 mg/m$^2$. In other embodiments, the second antibody dose of not more than about 10 mg/m$^2$, 50 mg/m$^2$, 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1,000 mg/m$^2$, 1,200 mg/m$^2$, 1,400 mg/m$^2$, 1,600 mg/m$^2$, 1,800 mg/m$^2$, 2,000 mg/m$^2$ or 2,200 mg/m$^2$. In further embodiments, the second antibody dose is in a range from about 10 mg/m$^2$-100 mg/m$^2$, 100 mg/m$^2$-200 mg/m$^2$, 200 mg/m$^2$-400 mg/m$^2$, 400 mg/m$^2$-600 mg/m$^2$, 600 mg/m$^2$-700 mg/m$^2$, 700 mg/m$^2$-800 mg/m$^2$, 800 mg/m$^2$-1,200 mg/m$^2$, 1,200 mg/m$^2$-1,600 mg/m$^2$ or 1,600 mg/m$^2$-2,200 mg/m$^2$. In preferred embodiments, for the treatment of pancreatic cancer, the second dose is about 600 mg/m$^2$, 700 mg/m$^2$, 1,000 mg/m$^2$, 1,400 mg/m$^2$, 1,800 mg/m$^2$ or 2,200 mg/m$^2$.

Alternately, the second antibody dose may be calculated based on specific patient characteristics such as the patient's age, gender, performance status, concurrent medical conditions, hepatic and renal sufficiency, tumor burden and other factors. Further, the second antibody dose may a standard antibody dose (mg/kg or mg/m$^2$) that is then "personalized" to account for patient-specific characteristics as discussed above.

In other embodiments, the second anti-CTGF antibody dose is sufficient to achieve an antibody concentration in blood of at least 0.5 µg/ml, 1 µg/ml, 5 µg/ml, 10 µg/ml, 15 µg/ml, 20 µg/ml, 25 µg/ml, 50 µg/ml, 75 µg/ml, 100 µg/ml, 125 µg/ml, 150 µg/ml or 200 µg/ml when measured about 2, 3, 4, 5, 6, 7, 8, 9, 10, 11, 12, 13, 14, 15, 16, 17, 18, 19, 20, 21, 22, 23, 24, or 28 days post-administration. In further embodiments, the second antibody dose is sufficient to achieve an antibody concentration in blood in the range of about 0.5 µg/ml-10 µg/ml, 10 µg/ml-20 µg/ml, 20 µg/ml-40 µg/ml, 40 µg/ml-60 µg/ml, 60 µg/ml-100 µg/ml, 100 µg/ml-150 µg/ml or 150 µg/ml-200 µg/ml when measured about 2, 3, 4, 5, 6, 7, 8, 9, 10, 11, 12, 13, 14, 15, 16, 17, 18, 19, 20, 21, 22, 23, 24, or 28 days post-administration. In preferred embodiments, for the treatment of pancreatic cancer, the second antibody dose is sufficient to achieve at least 80 µg/ml when measured about 14 days post-administration. In another preferred embodiment, a second antibody dose equal to or greater than 15 mg/kg is administered to produce a mean serum concentration of at least 80 µg/ml at 14 days post-administration that is effective to treat a CTGF-associated cancer.

In further embodiments, the second anti-CTGF antibody dose is sufficient to achieve an antibody concentration of at least 1 µg/ml/m$^2$, 5 µg/ml/m$^2$, 10 µg/ml/m$^2$, 20 µg/ml/m$^2$, 25 µg/ml/m$^2$, 30 µg/ml/m$^2$, 40 µg/ml/m$^2$, 45 µg/ml/m$^2$, 50 µg/ml/m$^2$, 60 µg/ml/m$^2$, 75 µg/ml/m$^2$, 80 µg/ml/m$^2$, 100 µg/ml/m$^2$ or 120 µg/ml/m$^2$, when measured about 7, 8, 9, 10, 11, 12, 13, 14, 15, 16, 17, 18, 19, 20, 21, 22, 23, 24, or 28 days post-administration. In other embodiments, the second antibody dose is sufficient to achieve an antibody concentration not more than about 30 µg/ml/m$^2$, 40 µg/ml/m$^2$, 45 µg/ml/m$^2$, 50 µg/ml/m$^2$, 60 µg/ml/m$^2$, 75 µg/ml/m$^2$, 80 µg/ml/m$^2$ or 100

µg/ml/m² when measured about 7, 8, 9, 10, 11, 12, 13, 14, 15, 16, 17, 18, 19, 20, 21, 22, 23, 24, or 28 days post-administration. In further embodiments, the second antibody dose is sufficient to achieve an antibody concentration in the range of about 1 µg/ml/m²-10 µg/ml/m², 10 µg/ml/m²-25 µg/ml/m², 25 µg/ml/m²-40 µg/ml/m², 40 µg/ml/m²-60 µg/ml/m², 60 µg/ml/m²-75 µg/ml/m² or 75 µg/ml/m²-100 µg/ml/m² or 100 µg/ml/m²-120 µg/ml/m² when measured about 7, 8, 9, 10, 11, 12, 13, 14, 15, 16, 17, 18, 19, 20, 21, 22, 23, 24, or 28 days post-administration. In preferred embodiments, for the treatment of pancreatic cancer, the second antibody dose is sufficient to achieve an antibody concentration of at least 50 µg/ml/m², 60 µg/ml/m², 70 µg/ml/m², 80 µg/ml/m², 100 µg/ml/m² or 120 µg/ml/m² when measured 14 days post-administration.

In further embodiments, the second antibody dose is sufficient to achieve an antibody exposure of at least 1,000 µg*h/ml, 5,000 µg*h/ml, 10,000 µg*h/ml, 20,000 µg*h/ml, 40,000 µg*h/ml, 60,000 µg*h/ml, 80,000 µg*h/ml, 100,000 µg*h/ml, 120,000 µg*h/ml, or 140,000 µg*h/ml. In some embodiments, the AUC is calculated from about 0-4 days, 0-5 days, 0-6 day, 0-7 days, 0-8 days, 0-9 days, 0-10 days, 0-11 days, 0-12 days, 0-13 days, 0-14 days, 0-16 days, 0-18 days 0-21 days, or 0-28 days. In particular embodiments, for the treatment of pancreatic cancer, the second antibody dose is sufficient to achieve an antibody exposure of at least 80,000 µg*h/ml for the time period of 0-14 days (0-336 hours) following second antibody administration.

In further embodiments, the first anti-CTGF antibody dose is a loading dose. The term "loading dose" as used herein refers to an initial antibody dose administered within a set time period to rapidly achieve a desired pharmacological antibody level. For example, a loading dose in reference to the methods of the invention may refer to an initial dosing regimen that rapidly increases the blood concentration of an anti-CTGF antibody to a pharmaceutically active level. The loading dose can be administered as a single injection or infusion, or alternatively, the loading dose can be administered as multiple antibody injections or infusion within a set time frame, e.g., three infusions of 15 mg/kg spaced over one week for a total infusion of 45 mg/kg. Depending on the amount of antibody required and the concentration of antibody in the formulation, the splitting of the desired antibody dose into two or more administrations may be necessary to avoid fluid overload or other complications. In some embodiments, the loading dose comprises 1, 2, 3 or 4 injections and/or infusions delivered over the course of 1, 2, 3, 4, 5, 6, 7, 8, 9, 10, 11, 12, 13 or 14 days to achieve a total accumulated loading dose.

In some embodiments, a pharmaceutically active level achieved with the loading dose comprises a level that is sufficient to induce stasis or a reduction of tumor cell growth; stasis or reduction of tumor cell motility and/or invasiveness; stasis or reduction of tumor size or volume, stasis or reduction of tumor metabolism as measured by $^{118}$ FDG PET, magnetic resonance spectroscopic imaging or other suitable modalities.

In some embodiments, the loading dose is at least 0.5 mg/kg, 1.0 mg/kg, 2.0 mg/kg, 3.0 mg/kg, 4.0 mg/kg, 5.0, mg/kg, 6.0 mg/kg, 7.0 mg/kg, 8.0 mg/kg, 9.0 mg/kg, 10 mg/kg, 12.5 mg/kg, 15 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In preferred embodiments, for the treatment of pancreatic cancer, the loading dose is about 15 mg/kg, 17.5 mg/kg, 22.5 mg/kg, 25 mg/kg, 35 mg/kg 45 mg/kg or 55 mg/kg.

In other embodiments, the loading dose is the antibody dose that is sufficient to achieve an antibody concentration in blood of at least 10 µg/ml, 25 µg/ml, 30 µg/ml, 40 µg/ml, 50 µg/ml, 60 µg/ml, 75 µg/ml, 75 µg/ml, 100 µg/ml, 125 µg/ml, 150 µg/m, 200 µg/ml, 300 µg/ml, 400 µg/ml or 500 µg/ml when measured about 14 days post-administration. In preferred embodiments, for the treatment of pancreatic cancer, the loading dose is the antibody dose sufficient to achieve an antibody blood concentration of at least 150 µg/ml when measured 14 days post-administration.

In some embodiments, the second antibody dose is a maintenance dose. The term "maintenance dose" as used herein refers to an antibody dose sufficient to maintain a desired physiologic or clinical response that was achieved with the loading dose. For example, a maintenance dose refers to a dosing regimen that maintains an anti-CTGF antibody induced response, for example, stasis or reduction of tumor cell growth; stasis or reduction in tumor cell motility; stasis or reduction of tumor size or volume, stasis or reduction of tumor metabolism as measured by $^{18}$ FDG PET, magnetic resonance spectroscopic imaging or other suitable modalities; or maintenance of disease remission. In some embodiments, the maintenance dose is lower than the loading dose. In other embodiments, the maintenance dose is the same as the loading dose, while in further embodiments, the maintenance dose is higher than the loading dose. The maintenance dose can be administered as a single injection or infusion, or alternatively, the maintenance dose can be administered as multiple antibody injections or infusion within a set time frame. In some embodiments, the maintenance dose comprises 1, 2, 3 or 4 injections and/or infusions delivered over the course of 1, 2, 3, 4, 5, 6, 7, 8, 9, 10, 11, 12, 13, 14, 18 or 21 days to achieve a total accumulated maintenance dose. Typically, maintenance doses are administered at regularly spaced intervals, for instance, every 1, 2, 4, 6, 8, 10, or 12 weeks.

In some embodiments, the maintenance dose is administered at least 1, 2, 3, 4, 5, 6, 7, 8, 10, 12, 16, 20 or 24 weeks post-administration of the loading dose. In other embodiments, the maintained dose is administered no more than about 1, 2, 3, 4, 5, 6, 7, 8, 10, 12, 16, 20 or 24 weeks post-administration of the loading dose. In further embodiments, the maintenance dose is administered within about 1-2 weeks, 1-3 weeks, 2-3 weeks, 2-4 weeks, 3-6 weeks, 4-8 weeks, 5-10 weeks, 6-12 weeks, 10-20 weeks or 12-25 weeks post-administration of the loading dose.

In some embodiments, multiple anti-CTGF antibody doses, including multiple maintenance doses, are administered. In further embodiments, the multiple antibody doses are administered as repeating treatment cycles with a scheduled period of rest in between successive treatment cycles. In some embodiments, the treatment cycles are at least 1, 2, 3, 4, 5, 6, 8, 10, 12, 16 or 20 weeks in duration. In further embodiments at least 2, 3, 4, 5, 6, 8, 10, 12, 15 or 20 treatment cycles are administered. In other embodiments, the rest break is of at least 1, 2, 3, 4, 5, 6, 8, 10, 12, 16 or 20 weeks in duration. In additional embodiments, the rest break is no more than about 1, 2, 3, 4, 5, 6, 8, 10, 12, 16 or 20 weeks in duration. In further embodiments, the multiple antibody doses are administered in successive treatment cycles that do not have a regularly scheduled rest period, so that the treatment is essentially continuous.

In a preferred embodiment, in the context of the treatment of pancreatic cancer, a loading dose of about 35 mg/kg is administered that is followed one week later with a maintenance dose of 17.5 mg/kg. The maintenance can be repeated in one week treatment cycles as desired. In another preferred embodiment, a pancreatic cancer patient is administered a loading dose of about 45 mg/kg that is followed one week later with a maintenance dose of about 22.5 mg/kg. The maintenance dose can be repeated in one week treatment cycles as desired.

In some embodiments, the treatment method exposes the patient, in one treatment cycle, to at least 0.25 g, 0.5 g, 0.75 g, 1.0 g, 1.5 g, 2.0 g, 2.5 g, 3.0 g, 3.5 g, 4.0 g, 5.0 g, 6.0 g, 8.0 g or 10.0 g of anti-CTGF antibody. In other embodiments, the treatment method exposes the patient, in one treatment cycle, to not more than about 0.75 g, 1.0 g, 1.5 g, 2.0 g, 2.5 g, 3.0 g, 3.5 g, 4.0 g, 5.0 g, 6.0 g, 8.0 g or 10.0 g of an anti-CTGF antibody. In further embodiments, the treatment method exposes the patient, in one treatment cycle, to a range of about 0.5 g-1.0 g, 1.0-2.0 g, 2.0-3.0 g, 3.0-4.0 g, 4.0-5.0 g, 5.0-6.0 g, 6.0-8.0 g or 8.0-10.0 g of anti-CTGF antibody.

In one aspect of the invention, a method is provided for treating pancreatic cancer in a subject comprising administering in one antibody treatment cycle about 1.0 g, 1.5 g, 1.75 g, 2.5 g, 3.15 g or 3.85 g, of an anti-CTGF antibody as derived for a 70 kg standard man. Patients of other weights would have their antibody dose suitably adjusted. In some embodiments, the antibody treatment cycle is about 1 or 2 weeks in length.

In another aspect of the invention, methods are provided for administering an anti-CTGF antibody based on titrating the antibody level in a patient's blood (whole blood, plasma or serum) or other biologic sample (lymph fluid, cerebrospinal fluid, tissue biopsy, etc.). The term "titrating" encompasses the idea that achieving or exceeding a target antibody level in a patient is associated with improved clinical outcome or prognosis. Titration is accomplished by administering a first anti-CTGF antibody dose, measuring the antibody concentration in a first biologic sample obtained from the patient, comparing the first antibody concentration in the first biologic sample to a first target antibody concentration and then adjusting the quantity of antibody administered in a second antibody dose so that when a second biologic sample is obtained and measured for a second antibody concentration, the second antibody concentration will achieve or exceed the first target antibody concentration. Typically, the first and second biologic samples are obtained at substantially the same time point post the respective antibody administration. Usually, the first and second biologic samples are identical, i.e., blood samples.

Titration assures that every patient is administered an antibody dose that meets or exceeds an antibody concentration at a specific time point post-administration that is associated with a desired pharmalogical or clinical response. Titration accounts for the patient-specific differences in various factors such as quantity of antigen, access to antigen, tumor burden, degree of desmoplasia, rate of antibody catabolism, rate of antibody excretion and antibody half-life in addition to other patient-specific factors such as age, gender, other concurrent medical conditions and renal sufficiency. Patient biologic samples can have lower than expected antibody levels based on the level of accessible or free antigen (CTGF) in blood, normal tissue, tumor and tumor stroma. For example, an initial, large quantity of available antigen in blood can bind with the administered antibody and the resulting complex taken up by the liver and catabolized leading to a low antibody concentration level in blood at the time a biologic sample is obtained. Typically, the biologic sample is a blood sample, but other biologic samples are contemplated such as serous fluids from the peritoneal cavity, lungs, or heart; or cerebrospinal fluid; or a tissue or tumor biopsy or other surgical sample.

With the titration treatment method, the first biologic sample is obtained at about 2, 3, 4, 5, 6, 7, 8, 9, 10, 11, 12, 13, 14, 15, 16, 17, 18, 19, 20, 21, 24 or 28 days post-administration. In other embodiments, the first biologic sample is obtained no later than 2, 3, 4, 5, 6, 7, 8, 9, 10, 11, 12, 13, 14, 15, 16, 17, 18, 19, 20, 21, 24 or 28 days post-administration. In still further embodiments, the first biologic sample is obtain within the period of 2-14 days, 4-18 days, 7-21 days, 14-21 days or 21-28 days, post-administration. In other embodiments, the first biologic sample is obtained at or near the end of a treatment cycle. Alternately, the first biologic sample is obtained about 1, 2 or 3 days before the administration of the second antibody dose to allow sufficient time to measure the anti-CTGF antibody level in the sample. In some embodiments, the antibody level in the sample is substantially similar to the $C_{min}$ of the treatment cycle. In preferred embodiments, for the treatment of pancreatic cancer, the first biologic sample is obtained about 14 days post-administration of the first antibody. i.e., the end of the two week treatment cycle.

Next, the first antibody level is compared to a first target antibody level. The first target antibody level is empirically derived based on the analysis of past patient data where patients at or above the first target antibody level had better pharmacological responses or clinical outcomes compared to those patients that had lower antibody levels at the sample time point. In some embodiments, the improved patient outcome is increased TTP, increased PFS, increased DFS, increased OS, increased 1-year survival, reduced need for supportive care, reduced need for narcotics, increased mobility, increased performance status or increased patient quality of life. In some embodiments, the empirically derived target antibody level corresponds to the antibody level that induces stable disease (less than a 30% reduction or less than a 20% increase in the sum of the products of the longest diameters in representative measurable lesions), partial regression of disease (a 30% or greater reduction in the sum of the longest diameters in representative measurable lesions) or complete regression of disease.

In some embodiments, the first target antibody level is at least 0.5 µg/ml, 1 µg/ml, 5 µg/ml, 10 µg/ml, 15 µg/ml, 20 µg/ml, 25 µg/ml, 50 µg/ml, 75 µg/ml, 100 µg/ml, 125 µg/ml, 150 µg/ml, 200 µg/ml, 300 µg/ml, 400 µg/ml or 500 µg/ml. In other embodiments, the first target antibody level is not more than about 0.5 µg/ml, 1 µg/ml, 5 µg/ml, 10 µg/ml, 15 µg/ml, 20 µg/ml, 25 µg/ml, 50 µg/ml, 75 µg/ml, 100 µg/ml, 125 µg/ml, 150 µg/ml, 200 µg/ml, 300 µg/ml, 400 µg/ml or 500 µg/ml. In preferred embodiments, for the treatment of pancreatic cancer, the first target antibody level is at least 150 µg/ml.

If the first antibody level is at least as high as the first target antibody level, than the healthcare provider will administer a second antibody dose that is substantially similar to the first antibody dose. If, on the other hand, the patient's first antibody level is lower than a first target antibody level, then the healthcare provider will administer a second antibody dose that is higher than the first antibody dose and calculated to compensate for such factors that may be present in a particular patient such as increased antibody catabolism, increased antibody uptake and clearance by the liver, kidney or other normal organs, high tumor burden or high tumor uptake of antibody that may led to increased antibody depletion from the measured biologic sample. By increasing the amount of administered antibody in the second dose to a quantity calculated to meet or exceed the first target antibody level, the patient will have a greater chance of achieving an antibody level that is associated with a beneficial pharmacological or clinical response.

A pharmacological or clinical response includes stasis or reduction of tumor cell growth; stasis or reduction of tumor cell motility and/or invasiveness; stasis or reduction of tumor size or volume, stasis or reduction of tumor metabolism as measured by $^{18}$FDG PET, magnetic resonance spectroscopic imaging or other suitable modalities. A pharmacological or clinical response further includes an increase in the median survival, TTP, PFS, DFS or OS of treated patients. A pharmacological or clinical response in the context of pancreatic cancer also includes the reduction, amelioration or reversal of anorexia, weight loss, fatigue, jaundice, pain, including abdominal pain, analgesic or narcotic consumption, nausea, indigestion, diarrhea, bloating, malaise, itching, dehydration, loss of appetite or hyperglycemia. In preferred embodiments, for the treatment of pancreatic cancer, the second antibody dose is calculated to be sufficient to achieve at least 150 µg/ml in blood when measured about 14 days post-administration, i.e., at the end of a 2 week treatment cycle.

Following the administration of the second antibody dose that is calculated to achieve or exceed the first target antibody blood level, a second biologic sample is obtained and assayed for a second antibody level. This second antibody level is compared to a second target antibody level. If the patient's second antibody level is at least as high as the second target antibody level, then the next (third) administration will be of a substantially similar level of antibody compared to the second administered dose. If the second antibody level is below the second target antibody level, the healthcare provider will increase the amount of antibody in the third dose to compensate for antibody depletion, short half-life, etc., and thereby ensure that the third dose will achieve or exceed the second target antibody level.

The titration process can be continued in this iterative manner as required to treat or stabilize the disease, maintain remission, or cure the patient. Alternatively, the titration process is performed for a set number of titration cycles e.g., 2, 3, 4, 5, 6, 7, 8, 10, 12, 16, or 24 cycles.

In some embodiments, the target antibody level remains the same for each subsequent titration cycle, while in other embodiments, the target antibody level is varied over time. In some embodiments, the target antibody level may decrease over time. In further instances, the target antibody level may increase over time. For example, the target antibody level can be increased over time in a linear manner, e.g., the first target antibody level is set at about 150 µg/ml, the second target antibody level is set for about 200 µg/ml, the third target antibody level is set for about 250 µg/ml and so forth. In a slight variation, the target antibody level is increased in a linear manner for a set number of treatment cycles and then is held constant (flat) at this level for all subsequent treatment cycles.

In other embodiments, the target antibody level is increased in a staircase manner. For example, the first target antibody level is set at 15 µg/ml, the second target antibody level is set at 25 µg/ml, the third target antibody level is set at 25 µg/ml, the forth target antibody level is set at 45 µg/ml, the fifth target antibody level is set at 45 µg/m and so forth. In some embodiments, after reaching a particular target antibody level, the staircase increase may be stopped and all subsequent antibody target levels held at a particular target level. Alternately, the titration treatment schedule may incorporate pulses or ramping up and down of target antibody levels.

The titration treatment regimen may be modified through the inclusion of data obtained through other modalities such as tumor markers or $^{18}$FDG PET-based imaging of tumors. For instance, a patient that has reached a target antibody blood level, but the blood sample does not show an expected drop in a tumor marker, the subsequent antibody dose may be raised above the amount that would normally be administered in order to induce a measurable tumor response, e.g., a drop in a tumor marker level in a subsequent blood sample.

In alternate embodiments, the first target antibody blood level is selected based on a reduction in the level of at least one tumor marker, wherein the reduction of the tumor marker level achieved in patients at or above the first target antibody blood level is associated with a better clinical outcome compared to those patients that achieved a lower reduction of the tumor marker level. A better clinical outcome includes longer median survival, longer time to progression (TTP), longer progression-free survival (PFS), longer disease-free survival (DFS) or longer overall survival (OS) compared to patients with an antibody blood level below the first target antibody blood level.

Useful tumor markers include carcinoembryonic antigen (CEA), carbohydrate antigen 19-9 (CA 19-9), UL16 binding protein 2 (ULBP2), carcinoembryonic antigen-related cell adhesion molecule 1 (CEACAM1), MUC1, alpha-fetoprotein, apolipoprotein C-I (ApoC-I), apolipoprotein A-II (ApoA-II), pancreatic associated antigen (Span-1), CA50 antigen, DU-PAN-2, serum amyloid A, insulin-like growth factor-binding protein-1a (IGFBP-1a), M2-pyruvate kinase, alpha4GnT, NPC-1C, elastase-1, tissue polypeptide antigen (TPA) and tissue polypeptide-specific antigen (TPS). Tumor markers can be used singularly or in combination. In a preferred embodiment, the tumor marker is CA 19-9. In another preferred embodiment, the combination of tumor markers, CA 19-9, DU-PAN-2 and Span-1 is used Tumor markers provide a useful proxy for monitoring or measuring the efficacy of therapy particularly in tumors, such as pancreatic cancer, where a reduction in viable tumor cells may not be readily apparent based on changes in tumor size or volume because of slow clearance of nonviable tumor cells and the presence of fibrosis that prevent an appreciable reduction in tumor size or volume.

In some embodiments, the reduction in a tumor marker achieved with the administration of sufficient antibody to meet or exceed a first target antibody blood level is a reduction in the tumor marker by at least 10%, 20%, 30%, 40%, 50%, 60%, 70%, 80%, 90% or 95% compared to a baseline measurement taken before initiating anti-CTGF antibody treatment.

In some embodiments, the first target antibody blood level is selected based on a reduction in the concentration of CTGF, including CTGF fragments, in the blood, wherein the reduction in CTGF concentration achieved in patients at or above the first target antibody blood level is associated with a better clinical outcome compared to those patients that do not achieve as marked a reduction of CTGF concentration in blood. In some embodiments, the threshold CTGF concentration in blood associated with the first target antibody blood level is to a concentration below 20 ng/ml, 15 ng/ml, 10 ng/ml, 5 ng/ml, 1 ng/ml or 0.1 ng/ml. A better clinical outcome includes longer median survival, longer time to progression (TTP), longer progression-free survival (PFS), longer disease-free survival (DFS) or longer overall survival (OS) compared to patients that do not achieve a reduction of blood CTGF concentration that is below a threshold concentration. In a preferred embodiment, for the treatment of pancreatic cancer, the first target antibody blood level is associated with a reduction of CTGF concentration in blood to a level ≤10 ng/ml.

In some embodiments, an antibody treatment cycle, including an antibody titration cycle, may be combined with the treatment cycle of at least one additional therapeutic agent to form a combined treatment cycle. Within any particular combined treatment cycle, the administration of the antibody and at least one other agent can be simultaneously, or they can be administered sequentially. In some embodiments, the combined treatment cycle is at least 1, 2, 3, 4, 5, 6, 7, 8, 9, 10, 11, 12, or 16 weeks in duration and can be repeated as desired. In further embodiments, the combined treatment cycle is not more than about 2, 3, 4, 5, 6, 7, 8, 9, 10, 11, 12, or 16 weeks in duration. Alternately, the antibody treatment cycle may have a cycle schedule that is independent of the cycle schedule of another therapeutic agent.

Typically, when combined treatment cycles are used, a rest period is scheduled between sequential treatment cycles to allow a patient to recover from the effects of the therapy. In some embodiments, the rest period is at least 1, 2, 3, 4, 5, 6, 7, 8, 9, 10 or 12 weeks in duration. In other embodiments, the rest period is not more than about 1, 2, 3, 4, 5, 6, 7, 8, 9, 10 or 12 weeks in duration. In a preferred embodiment, the rest period is about 1 week in duration.

In another aspect of the invention, a method is provided to increase time to progression (TTP), progression-free survival (PFS), disease-free survival (DFS), overall survival (OS) or 1-year survival rate in a subject with a CTGF-associated cancer or desmoplastic cancer over that achieved with chemotherapy alone, the method comprises the addition of an effective amount of an anti-CTGF antibody to chemotherapy. In some embodiments, the addition of an effective amount of an anti-CTGF antibody to chemotherapy does not increase the number or severity of adverse events above that associated with chemotherapy alone. In some embodiments, the anti-CTGF antibody is administered at a dose of at least 0.5 mg/kg, 1.0 mg/kg, 2.0 mg/kg, 3.0 mg/kg, 4.0 mg/kg, 5.0, mg/kg, 6.0 mg/kg, 7.0 mg/kg, 8.0 mg/kg, 9.0 mg/kg, 10 mg/kg, 12.5 mg/kg, 17.5 mg/kg, 15 mg/kg, 17.5 mg/kg, 22.5 mg/kg, 25 mg/kg, 35 mg/kg, 45 mg/kg or 55 mg/kg.

In some embodiments, the addition of an effective amount of an anti-CTGF antibody to chemotherapy extends the TTP in subjects with a CTGF-associated cancer or desmoplastic cancer by at least 3.5, 4.0, 4.5, 5.0, 5.5, 6.0, 6.5, 7.0, 7.5, 8.0, 8.5, 9.0, 9.5, 10.0, 11, 12, 14, 16, 18, 20, 22 or 24 months. In particular embodiments, the addition of an effective amount of an anti-CTGF antibody to standard chemotherapy, i.e., gemcitabine or gemcitabine-based combination therapy, extends the TTP in subjects with a pancreatic cancer by at least 3.5, 4.0, 4.5, 5.0, 5.5, 6.0, 6.5, 7.0, 7.5, 8.0, 8.5, 9.0, 9.5, 10.0, 11, 12, 14, 16, 18, 20, 22 or 24 months. In alternate embodiments, the addition of an effective amount of an anti-CTGF antibody to standard chemotherapy, i.e., gemcitabine or gemcitabine-based combination therapy, extends the TTP in subjects with a pancreatic cancer by at least 10%, 20%, 30%, 40%, 50%, 60%, 70%, 80%, 90%, 100%, 125%, 150%, 175% or 200% longer than is achieved with standard therapy alone. In some embodiments, standard chemotherapy includes erlotinib. In preferred embodiments, the dose of anti-CTGF antibody that produces a median TTP of at least 5.0 months in advanced pancreatic cancer is at least 15 mg/kg, 17.5 mg/kg, 22.5 mg/kg, 25 mg/kg, 35 mg/kg, 45 mg/kg or 55 mg/kg.

In some embodiments, the addition of an effective amount of an anti-CTGF antibody to chemotherapy extends the PFS in subjects with a CTGF-associated cancer or desmoplastic cancer by at least 3.5, 4.0, 4.5, 5.0, 5.5, 6.0, 6.5, 7.0, 7.5, 8.0, 8.5, 9.0, 9.5, 10.0, 11, 12, 14, 16, 18, 20, 22 or 24 months. In particular embodiments, the addition of an effective amount of an anti-CTGF antibody to standard chemotherapy, i.e., gemcitabine or gemcitabine-based combination therapy, extends the PFS in subjects with pancreatic cancer by at least 10%, 20%, 30%, 40%, 50%, 60%, 70%, 80%, 90%, 100%, 125%, 150%, 175% or 200% longer than is achieved with standard therapy alone. In some embodiments, standard chemotherapy includes erlotinib. In preferred embodiments, the dose of anti-CTGF antibody that produces a median PFS of at least 5.0 months in advanced pancreatic cancer is at least 15 mg/kg, 17.5 mg/kg, 22.5 mg/kg, 25 mg/kg, 35 mg/kg, 45 mg/kg or 55 mg/kg.

In some embodiments, the addition of an effective amount of an anti-CTGF antibody to chemotherapy extends the OS in subjects with a CTGF-associated cancer or desmoplastic cancer by at least 10%, 20%, 30%, 40%, 50%, 60%, 70%, 80%, 90%, 100%, 125%, 150%, 175% or 200% longer than is achieved with chemotherapy alone. In particular embodiments, the addition of an effective amount of an anti-CTGF antibody to standard chemotherapy, i.e., gemcitabine or gemcitabine-based combination therapy, extends the OS in subjects with a pancreatic cancer by at least 10%, 20%, 30%, 40%, 50%, 60%, 70%, 80%, 90%, 100%, 125%, 150%, 175% or 200% longer than is achieved with standard chemotherapy alone. In further embodiments, the addition of an effective amount of anti-CTGF antibody to standard chemotherapy, i.e., gemcitabine or gemcitabine-based combination therapy, extends the OS in subjects with pancreatic cancer by at least 7.0, 7.5, 8.0, 8.5, 9.0, 9.5, 10.0, 11, 12, 13, 14, 15, 16, 18, 20, 22 or 24 months longer than is achieved with standard chemotherapy alone. In preferred embodiments, the dose of an anti-CTGF antibody that produces a median OS of at least 7.0 months in advanced pancreatic cancer is at least 15 mg/kg, 17.5 mg/kg, 22.5 mg/kg, 25 mg/kg, 35 mg/kg, 45 mg/kg or 55 mg/kg.

In some embodiments, the increase in TTP, PFS, DFS, OS, or 1-year survival rate achieved with the addition of an effective amount of an anti-CTGF antibody to chemotherapy for the treatment of a CTGF-associated cancer or desmoplastic cancer is achieved without a concomitant increase in the number or severity of adverse events above that associated with the chemotherapy alone. In some embodiments, the anti-CTGF antibody is administered at a dose of at least 15 mg/kg, 17.5 mg/kg, 22.5 mg/kg, 25 mg/kg, 35 mg/kg, 45 mg/kg or 55 mg/kg.

In particular embodiments, the treatment method increases TTP, PFS, DFS, OS, or 1-year survival rate in a subject with pancreatic cancer over that seen with the use of gemcitabine or gemcitabine-based combination chemotherapy without a corresponding increase in the number or severity of adverse events that are associated with gemcitabine or gemcitabine-based combination chemotherapy. In some embodiments, the subject has localized disease, while in other embodiments, the subject has advanced disease, including metastatic disease. The method comprises administering an anti-CTGF antibody in addition to gemcitabine or gemcitabine-based combination therapy to a subject with pancreatic cancer. In some embodiments, the pancreatic cancer is advanced. In other embodiments, the anti-CTGF antibody is administered at a dose of at least 15 mg/kg, 17.5 mg/kg, 22.5 mg/kg, 25 mg/kg, 35 mg/kg, 45 mg/kg or 55 mg/kg.

In some embodiments, the adverse event seen with gemcitabine therapy is reported as a WHO-graded adverse event. In further embodiments the WHO-graded adverse event is a laboratory defined adverse event. In other embodiments, the laboratory defined adverse event is a hematologic-, hepatic- or renal-associated adverse event. In still further embodiments, the hematologic-associated adverse event is anemia, leukopenia, neutropenia or thrombocytopenia. In other embodiments, the hepatic-associated adverse event is elevated alanine transaminase (ALT), elevated aspartate aminotransferase (AST), elevated alkaline phosphatase or elevated bilirubin. In further embodiments, the renal-associated adverse event is proteinuria, hematuria, elevated blood urea nitrogen (BUN) or elevated creatinine.

In some embodiments, the WHO-graded adverse event is a non-laboratory-associated adverse event. In further embodiments, the non-laboratory-associated adverse event is pain, fever, rash, dyspnea, constipation, diarrhea, hemorrhage, infection, alopecia, stomatitis, somnolence or paresthesia. In further embodiments, the adverse event is an allergic reaction, anorexia, dehydration, edema, fatigue or increased muscle weakness.

In another aspect of the invention, a method is provided to improve palliation of a cancer-associated symptom in a subject with a CTGF-associated cancer or desmoplastic cancer over the degree of palliation seen with chemotherapy or radiotherapy alone. In some embodiments, the improvement in palliation is achieved without a corresponding increase in the number or severity of adverse events associated with chemotherapy treatment. In some embodiments, the CTGF-associated cancer is pancreatic cancer. In further embodiments, the improvement in palliation of a pancreatic cancer-associated symptom is an improvement over that achieved with the use of gemcitabine alone or gemcitabine-based combination therapy. In other embodiments, the improvement in palliation in pancreatic cancer is achieved without a corresponding increase in the severity of an adverse event associated with gemcitabine or gemcitabine-based combination therapy. In some embodiments, the anti-CTGF antibody is administered at a dose of at least 15 mg/kg, 17.5 mg/kg, 22.5 mg/kg, 25 mg/kg, 35 mg/kg, 45 mg/kg or 55 mg/kg.

In some embodiments, the pancreatic cancer symptom to be palliated is selected from the group consisting of anorexia, weight loss, fatigue, jaundice, pain, including abdominal pain, nausea, indigestion, diarrhea, bloating, malaise, itching, dehydration, loss of appetite or hyperglycemia.

In some embodiments, the adverse event seen with gemcitabine therapy is reported as a WHO-graded adverse event. In further embodiments the WHO-graded adverse event is a laboratory defined adverse event. In other embodiments, the laboratory defined adverse event is a hematologic-, hepatic- or renal-associated adverse event. In still further embodiments, the hematologic-associated adverse event is anemia, leukopenia, neutropenia or thrombocytopenia. In other embodiments, the hepatic-associated adverse event is elevated alanine transaminiase (ALT), elevated aspartate aminotransferase (AST), elevated alkaline phosphatase or elevated bilirubin. In further embodiments, the renal-associated adverse event is proteinuria, hematuria, elevated blood urea nitrogen (BUN) or elevated creatinine.

In some embodiments, the WHO-graded adverse event is a non-laboratory-associated adverse event. In further embodiments, the non-laboratory-associated adverse event is pain, fever, rash, dyspnea, constipation, diarrhea, hemorrhage, infection, alopecia, stomatitis, somnolence or paresthesia. In further embodiments, the adverse event is an allergic reaction, anorexia, dehydration, edema, fatigue or increased muscle weakness.

In another aspect, the invention provides a method to decrease pain intensity, decrease analgesic or narcotic consumption, increase performance status or increase the weight gain in a patient with advanced pancreatic cancer over that seen with the use of gemcitabine alone, without a corresponding increase in the severity of an adverse event associated with gemcitabine therapy. In some embodiments, the anti-CTGF antibody is administered at a dose of at least 15 mg/kg, 17.5 mg/kg, 22.5 mg/kg, 25 mg/kg, 35 mg/kg, 45 mg/kg or 55 mg/kg. In some embodiments, the reduction in pain intensity is at least a 50% reduction in pain intensity measured using the Memorial Pain Assessment Card. In another embodiment, the improvement in performance status is at least a 10, 20 or 30 point improvement as measured using the Karnofsky Performance Scale. In some embodiments, the improvement extends at least 2, 3, 4, 5 or 6 consecutive weeks. In a further embodiment, the increase in weight is at least a 3%, 4%, 5%, 6%, 7%, 8%, 9% or 10% weight gain not due to fluid accumulation.

In another aspect of the invention, a method is provided to increase the health-related quality of life (HRQL) of a subject with advanced pancreatic cancer over that seen with the use of gemcitabine alone, without a corresponding increase in the severity of an adverse event associated with gemcitabine therapy. In some embodiments, the anti-CTGF antibody is administered at a dose of at least 15 mg/kg, 17.5 mg/kg, 22.5 mg/kg, 25 mg/kg, 35 mg/kg, 45 mg/kg or 55 mg/kg. In some embodiments, the HRQL assessment is performed using a measuring system that is substantially similar to the Functional Assessment of Cancer Therapy (FACT) measurement system. In one embodiment, the HRQL assessment comprises a component that is substantially similar to FACT-G, a 27-item self-report instrument that assesses the following dimensions of HRQL: physical status, emotional well-being, functional well-being, family/social issues, sexuality/intimacy, work status, and future orientation. These 27 general questions are applicable to patients with all types of cancer. In another embodiment, the HRQL assessment has a pancreatic cancer-specific subsection of the measurement system. In a preferred embodiment, the pancreatic cancer-specific subsection of the measurement system comprises or is substantially similar to the European Organization for the Research and Treatment of Cancer (EORTC) QLQ-PAN 26, a 26 item questionnaire for pancreatic cancer patients.

In another aspect of the invention, a method is provided to potentiate a chemotherapy agent, immunotherapy agent or radiotherapy treatment, the method comprising adding an effective amount of anti-CTGF antibody to the chemotherapy agent, immunotherapy agent or radiotherapy treatment. In some embodiments, the addition of an anti-CTGF antibody increases the therapeutic efficacy of a chemotherapy agent, immunotherapy agent or radiotherapy treatment by at least 10%, 20%, 30%, 40%, 50%, 60%, 70%, 80% or 90%. In some embodiments, the increase in therapeutic efficacy is achieved without additional toxicity. In some embodiments, the addition of the anti-CTGF antibody allows for the use of a reduced quantity of chemotherapy agent, immunotherapy agent or radiation to achieve substantially the same or greater therapeutic activity as seen with standard quantity of chemotherapy agent, immunotherapy agent or radiation. In further embodiments, the achievement of substantially the same or greater therapeutic activity as seen with standard quantity of chemotherapy agent, immunotherapy agent or radiation, while using a reduced amount a chemotherapy agent, immunotherapy agent or radiation is achieved without additional occurances or severity of adverse events. In some embodiments, the anti-CTGF antibody is administered at a dose of at least 0.5 mg/kg, 1.0 mg/kg, 2.0 mg/kg, 3.0 mg/kg, 4.0 mg/kg, 5.0, mg/kg, 6.0 mg/kg, 7.0 mg/kg, 8.0 mg/kg, 9.0 mg/kg, 10 mg/kg, 12.5 mg/kg, 17.5 mg/kg, 15 mg/kg, 17.5 mg/kg, 22.5 mg/kg, 25 mg/kg, 35 mg/kg, 45 mg/kg or 55 mg/kg.

In one aspect of the invention, an anti-CTGF antibody is provided for use in treating a CTGF-associated cancer in a subject, wherein the subject has a pretreatment CTGF blood level of less than or equal to10 ng/ml. In some embodiments, subjects with pretreatment blood levels of CTGF≤10 ng/ml have greater tumor responses when treated with an anti-CTGF antibody compared to subjects that have pretreatment blood levels of CTGF>10 ng/ml. In certain instances, it may be advantageous to screen patients for low blood levels of CTGF to select patients that are likely to have a greater tumor response when treated with an anti-CTGF antibody.

In another aspect of the invention, an anti-CTGF antibody is provided for use in treating a CTGF-associated cancer is a subject, wherein the antibody is for reducing or depleting circulating CTGF. In some instances, the reduction or depletion of CTGF in blood is associated with improved therapeutic outcomes. In some embodiments, the administration of the anti-CTGF antibody reduces a subject's blood level of CTGF by at least 10%, 20%, 30%, 40%, 50%, 60%, 70%, 80% or 90% compared to a pretreatment CTGF blood level.

In another aspect of the invention, an anti-CTGF antibody is provided for use in treating a CTGF-associated cancer in a subject, wherein the antibody is administered in an amount that results in at least a 10%, 20%, 30%, 40%, 50%, 60%, 70%, 80% or 90% reduction in the pretreatment blood level of a tumor marker. In some embodiments, a reduction by the blood level of a tumor marker is associated with an improved therapeutic outcome. In further embodiments, the tumor marker is selected from the group consisting of carcinoembryonic antigen (CEA), carbohydrate antigen 19-9 (CA 19-9), UL16 binding protein 2 (ULBP2), carcinoembryonic antigen-related cell adhesion molecule 1 (CEACAM1), MUC1, alpha-fetoprotein, apolipoprotein C-I (ApoC-I), apolipoprotein A-II (ApoA-II), pancreatic associated antigen (Span-1), CA50 antigen, DU-PAN-2, serum amyloid A, insulin-like growth factor-binding protein-1a (IGFBP-1a), M2-pyruvate kinase, alpha4GnT, NPC-1C, elastase-1, tissue polypeptide antigen (TPA) and tissue polypeptide-specific antigen (TPS).

In a further aspect of the invention, an anti-CTGF antibody is provided for use in treating a CTGF-associated cancer in a subject, wherein the subject's cancer is an advanced cancer, i.e., spread beyond the tissue or organ of origin. Advanced pancreatic cancer includes cancers classified as Stage IIA (a tumor that is growing outside the pancreas but not into large blood vessels); Stage IIB (a tumor that is either confined to the pancreas or growing outside the pancreas that has further spread to nearby lymph nodes, but not into nearby large blood vessels or major nerves); Stage III (a tumor that is growing outside the pancreas into nearby large blood vessels or major nerves and may also have spread to nearby lymph nodes); and Stage IV (metastatic disease). Peritoneal carcinamatosis, the regional spread of cancer cells throughout the peritoneal cavity as also included as an advanced cancer. In some embodiments, the subject's pancreatic cancer is Stage IIA, Stage IIB, Stage III or Stage IV. In some embodiments, the subject with advanced cancer has the primary tumor mass surgically excised or treated with radiation therapy before or concurrently with anti-CTGF antibody therapy.

In another aspect of the invention, an anti-CTGF antibody is provided for use in treating a CTGF-associated cancer in a subject, wherein the antibody is for reducing the metabolic activity of a tumor. In some embodiments, the metabolic activity is measured using $^{18}$FDG-PET. In some instances, the reduction in a tumor's metabolic rate is associated with improved therapeutic outcomes. In some embodiments, the administration of the anti-CTGF antibody reduces a tumor's metabolic activity by at least 10%, 20%, 30%, 40%, 50%, 60%, 70%, 80% or 90% compared to a pretreatment measurement.

Therapeutic Agents

The methods of the present invention utilize anti-CTGF antibodies. Exemplary antibodies for use in the methods of the present invention are described, e.g., in U.S. Pat. No. 5,408,040; International Publication No. WO 99/07407 (PCT/US1998/016423); International Publication No. WO 00/35936 (PCT/US1999/029652); and International Publication No. WO 99/33878. Preferably, the anti-CTGF antibody for use in the method is a monoclonal antibody. Preferably the antibody is a neutralizing antibody. In other preferred embodiments, the antibody is a human or humanized antibody to CTGF. In a more preferred embodiment, the antibody recognizes an epitope within domain 2 of human CTGF. Exemplary monoclonal anti-CTGF antibodies for use in the methods of the present invention include CLN1 or mAb1 described in U.S. Pat. No. 7,405,274. In a particular embodiment, the antibody is CLN1, as described in U.S. Pat. No. 7,405,274. In a particular embodiment, the antibody is the antibody produced by ATCC Accession No. PTA-6006 cell line, as described in U.S. Pat. No. 7,405,274. Variants of CLN1 that retain the binding and neutralization functions characteristic of CLN1 are also useful in the present invention. Such variants typically retain the variable regions of the heavy and/or light chain of the original neutralizing antibody, or minimally the complementarity determining regions (CDR) of heavy and light chains, and may contain substitutions and/or deletions in the amino acid sequences outside of those variable regions. Fragments and engineered versions of the original neutralizing antibody, e.g., Fab, F(ab)2, Fv, scFV, diabodies, triabodies, minibodies, nanobodies, chimeric antibodies, humanized antibodies, etc. are likewise useful in the method of the present invention as are antibody mimetics. Such antibodies, or fragments thereof, can be administered by various means known to those skilled in the art. For example, antibodies are often injected intravenously, intraperitoneally, or subcutaneously.

Accordingly, in certain embodiments of the present invention, the anti-CTGF agent is an anti-CTGF antibody. In a preferred embodiment, the anti-CTGF antibody is a monoclonal antibody. In a particularly preferred embodiment, the antibody is a neutralizing antibody. In another preferred embodiment, the antibody is a human or humanized antibody to CTGF. In a more preferred embodiment, the antibody recognizes an epitope within domain 2 of CTGF. In a particular embodiment, the antibody is CLN1, as described in U.S. Pat. No. 7,405,274. In a particular embodiment, the antibody is the antibody produced by ATCC Accession No. PTA-6006 cell line, as described in U.S. Pat. No. 7,405,274.

In some embodiments, an additional therapeutic agent is administered. In further embodiments the additional therapeutic agent is a chemotherapy agent. As used herein, the term "chemotherapeutic agent" refers to any compound that can be used in the treatment, management or amelioration of cancer, including CTGF-associated cancers, desmoplastic cancers or pancreatic cancer, or the amelioration or relief of one or more symptoms of a cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycins, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, fioxuridine; androgens such as calusterone, dromostanolone propionate, epitiostanol, mepitiostane, testolactone; anti-adrenals such as aminoglutethimide, mitotane, trilostane; frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2'2"-trichlorotriethylamine; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; chlorambucil; gemcitabine; 6-thioguanine; mercaptopurine; methotrexate; platinum analogs such as cisplatin and carboplatin; etoposide (VP-16); ifosfamide; mitomycin C; mitoxantrone; vinblastine; vincristine; vinorelbine; navelbine; novantrone; teniposide; daunomycin; aminopterin; xeloda; ibandronate; difluoromethylornithine (DMFO); retinoic acid; esperamicins; capecitabine; imexon; tyrosine kinase inhibitors, such as epidermal growth factor receptor tyrosine kinase inhibitor erlotinib; and pharmaceutically acceptable salts, acids or derivatives of any of the above. In particular embodiments, the chemotherapeutic agent is gemcitabine, erlotinib or both. In other embodiments, the chemotherapeutic agent is capecitabine. In further embodiments, the combined chemotherapeutic agents, 5-fluorouracil, leucovorin, irinotecan and oxaliplatin (FOLFIRINOX) are used. In still other embodiments, the combined chemotherapy agents are gemcitabine, docetaxel and capecitabine (GTX). In further embodiments, one or more chemotherapy agent is combined with concurrent radiotherapy. In particular embodiments, 5-fluorouracil is combined with concurrent radiotherapy.

In some embodiments, the additional therapeutic agent is an immunotherapy agent Immunotherapy agent is defined broadly to include exogenously produced antibodies, such as anti-human extracellular matrix metalloproteinase inducer (EMMPRIN) antibody or bispecific T cell engaging antibody MT110; vaccines, including, peptide vaccines, whole tumor cell vaccines, antigen-pulsed dendritic cell-based vaccines and DNA vaccines; and adoptive cell transfer.

In still further embodiments, the additional therapeutic agent is selected from the group consisting of oncolytic viruses, such as HF10; ultrasound-guided high-intensity focused ultrasound therapeutic ablation; brachytherapy seeds; antisense oligonucleotides and siRNA to membrane-type 1 matrix metalloproteinase (MT1-MMP), CTGF, TGF-β or Smad.

The methods of the present invention are applicable to all patients that have CTGF-associated cancer. Patients include those with localized tumors, tumors that have invaded into surrounding tissue or organs, tumors that have spread to the peritoneal cavity (peritoneal carcinomatosis) and also tumor metastases. With respect to pancreatic cancer, the disclosed anti-CTGF therapy is applicable to all stages of the disease from Stage I-Stage IVB and including cancer recurrences. Anti-CTGF antibodies can be administered using the disclosed methodologies as front-line therapy, including in combination with agents that represent the current standard of care; as a neoadjuvant prior to surgery, and as second-line or salvage therapy following unresponsiveness to first-line therapies or cancer recurrence. Furthermore, the disclosed methodologies can be used to administer an anti-CTGF antibody as a maintenance therapy following the induction of a complete response that is achieved with any type of therapy. For example, patients with local disease that achieve a complete response following surgery can be treated using the disclosed methodologies in order to maintain the complete response. Use of an anti-CTGF antibody may suppress or inhibit the growth of micrometastases present before surgery and also suppress or inhibit the growth of cancer cells shed during surgery.

Pharmaceutical Formulations and Routes of Administration

The compositions and compounds suitable for use in the method, or for manufacture of a medicament, of the present invention can be delivered directly or in pharmaceutical compositions containing excipients, as is well known in the art.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a suitable compound for use in the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound for use in the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions for use in the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro)-emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., treatment of cancer, including induction of anti-tumor effects, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

In some embodiments, the patient is administered an anti-CTGF antibody at least once per treatment cycle. In other embodiments, multiple administrations of the anti-CTGF antibody are given per treatment cycle. In further embodiments, the treatment cycle is designed to achieve a threshold circulating antibody concentration in the patient. In some embodiments, a first dose of an anti-CTGF antibody is administered and immediately preceding the administration of a second dose of antibody, a blood sample is drawn and analyzed for anti-CTGF antibody concentration. The blood concentration is then compared to a first target antibody blood level. Based on the patient's age, gender, body mass index, tumor burden, general medical condition and related factors a second antibody dose is administered that is calculated to meet or exceed a second target antibody blood level.

In effect, the anti-CTGF antibody dose is being titrated in the individual patient to achieve an empirically derived antibody Cmin level that is associated with improved patient outcome. In some embodiments, the improved patient outcome is increased time to disease progression, increased disease free survival, increased overall survival, reduced need for supportive care, reduced need for narcotics, increased mobility, increased performance status or increased patient quality of life. In some embodiments, the empirically derived antibody Cmin level corresponds to stable disease, partial regression of disease or complete regression of disease.

In some embodiments, the first antibody dose is at least 500 mg/m², while in other embodiments, the first antibody doses is at least 600 mg/m², 800 mg/m², 1,000 mg/m², 1,200 mg/m², 1,500 mg/m² or 2,000 mg/m². In some embodiments, the first dose of the antibody is at least 15 mg/kg, 20 mg/kg, 25 mg/kg, 30 mg/kg, 40 mg/kg, 50 mg/kg or 100 mg/kg.

In some embodiments, the measurement of $C_{min}$ for the first antibody dose is made about 7, 8, 9, 10, 11, 12, 13, 14, 15, 16, 17, 18, 19, 20, 21, 22, 23, 24, 25, 26, 27 or 28 days post-administration. In other embodiments, the Cmin for the first antibody dose is made about 1 week, 2 weeks, 3 weeks or 4 weeks post-administration. In some embodiments, the Cmin concentration of anti-CTGF antibody in the patient's blood is compared to a first target blood level. In some embodiments, the first target blood level is at least about 50 µg/ml, 75 µg/ml, 100 µg/ml, 125 µg/ml, 150 µg/ml or 200 µg/ml.

In further embodiments, a second antibody dose of administration is administered that is followed by a second blood measurement of blood antibody level. The blood level of the antibody seen in the second sample is then compared to a second target blood level. Depending upon the therapeutic intent, a third antibody dose is calculated to achieve the second target blood level or a higher blood level. Treatment can be continued using the same, iterative process as required to treat, stabilize, or cure the patient.

Articles of Manufacture

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In one embodiment, an article of manufacture is provided comprising: A) a container comprising an anti-CTGF antibody; and B) a package insert with instructions for treating pancreatic cancer, wherein the instructions indicate that a dose of the anti-CTGF antibody of about 1.0 g to 4.0 g is administered to the patient per two week treatment cycle.

In another embodiment, the invention provides an article of manufacture comprising: (a) a container comprising an anti-CTGF antibody; and (b) a package insert with instructions for treating pancreatic cancer in a subject, wherein the instructions indicate that an amount of the antibody is administered to the subject that is effective to provide an initial antibody exposure of at least 80,000 µg*h/ml ($AUC_{0-336\ hours}$) followed by a second antibody dose, that is effective to provide an second antibody exposure of at least 80,000 µg*h/ml ($AUC_{0-336\ hours}$). In further embodiments, the second antibody dose is not provided until about 2 to 8 weeks from the initial antibody administration.

In a further embodiment, the article of manufacture further comprises a container comprising a second medicament, wherein the anti-CTGF antibody is a first medicament. This article further comprises instructions on the package insert for treating the patient with the second medicament, in an effective amount. The second medicament may be a chemotherapeutic agent or an immunotherapy agent. The preferred second medicament is gemcitabine or erlotinib.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

Anti-CTGF Antibody Dose Finding Study in Advanced Pancreatic Cancer

Seventeen chemotherapy-naïve patients with unresectable pancreatic cancer were treated every 2 weeks with CLN1 antibody at 3 (n=4), 10 (n=3), or 15 (n=10) mg/kg. All patients were also given standard of care therapy with gemcitabine (at 1000 mg/m² dosed every week for 3 weeks, one week off, and repeated) and erlotinib (dosed continually at 100 mg) starting at day 15, concomitant with administration of the second dose of CLN1. A safety monitoring committee determined whether escalation to the next dose level is permitted. Assessments of tumor response measured by CT were made according to Response Evaluation Criteria in Solid Tumors 1.0 (RECIST 1.0) guidelines at baseline and every 8 weeks. For dose cohorts of 15 mg/kg and higher, tumor metabolic activity was measured by PET at baseline and day 14 (prior to administration of the first dose of chemotherapy).

Results

The administrations of CLN1 were well tolerated with no safety signals detected when used as a single agent. Steady-state $C_{max}$ (median 428, range 236-455 µg/ml) and $T_{1/2}$ (median 6.6, 6.3-6.7 days) at 10 mg/kg dose level were comparable to PK data from subjects in non-oncological trials who received CLN1 at the same dose level. Table 1 shows the time to half-life values for all dose levels to date.

TABLE 1

PHARMACOKINETICS

| | CLN1 Dose Administration Day 1 and Day 43 Estimated $t_{1/2}$ (days) | | | |
|---|---|---|---|---|
| Dose | Day 1 Mean | Day 1 Median | Day 43 Mean | Day 43 Median |
| 3 mg/kg | 3.1 | 3.3 | 2.6 | 2.6 |
| 10 mg/kg | 4.6 | 4.8 | 6.5 | 6.6 |
| 15 mg/kg | 5.4 | 4.8 | 7.4 | 7.0 |

For the patients treated with 3, 10, or 15 mg/kg, median time to progression (TTP) is 4.7 months and median overall survival (OS) is 9.1 months. Table 2 shows the data in more detail.

TABLE 2

Survival Data

| (n = 15): | Modified ITT (months) | Range (months) |
|---|---|---|
| Median Time to Progression: | | |
| 3 mg/kg | 4.5 | 1.2-5.8 |
| 10 mg/kg | 3.7 | 3.1-6.0 |
| 15 mg/kg | 7.7 | 1.9-13.9+ |
| All Cohorts | 4.7 | 1.2-13.9+ |
| Median Overall Survival: | | |
| 3 mg/kg | 9.1 | 1.2-9.3 |
| 10 mg/kg | 6.5 | 4.1-10.7 |
| 15 mg/kg | 9.4 | 1.9-13.9+ |
| All Cohorts | 9.1 | 1.2-13.9+ |

The best response according to RECIST indicated that one patient had a partial response, 9 patients had stable disease, 2 patients progressed, and 3 were not evaluable having discontinued the trial for reasons unrelated to treatment with CLN1 before CT imaging at week 8. Data in Table 3.

TABLE 3

BEST RESPONSE BY RECIST V1.0

| Modified ITT (n = 15): | PR | SD | PD | NE* |
|---|---|---|---|---|
| 3 mg/kg | 0 | 1 | 1 | 1 |
| 10 mg/kg | 0 | 3 | 0 | 0 |
| 15 mg/kg | 1 | 5 | 1 | 2 |
| Total: | 1 | 9 | 2 | 3 |

*NE (not evaluable) patients discontinued treatment prior to CT imaging at the 8 week point.

In the highest dose cohort (15 mg/kg), 5 of 5 patients showed reduced metabolic activity in the primary tumor as measured by PET after having received one dose of antibody and prior to initiating chemotherapy demonstrating that as a single-agent, CLN1 exerts a biological effect on the tumor. See Table 4. Three of these 5 patients showed a partial metabolic response (defined as ≥15% reduction after a single dose of drug). One patient with a partial response to the combined treatment according to RECIST continued to have tumor regression past 13.6 months with complete metabolic response in the primary tumor, and a decrease in the biomarker CA 19-9 from ≥2000 U/L to level sustained below 60 U/L.

TABLE 4

CLN1 SINGLE-AGENT ACTIVITY BY PET

| Patient | Lesion Location | Baseline SUV* | Day 14 SUV | TTP (months) |
|---|---|---|---|---|
| 0009 | Pancreas | 6.6 | 4.5 | 13.9+ |
| | Left Lower Lung | 3.7 | 2.6 | |
| | Right Lower Lung | 3.0 | 1.8 | |
| 0010 | Pancreas | 9.4 | 6.3 | 7.7 |
| | Pelvic Nodule | 5.4 | 2.5 | |
| | Peritoneal Nodule | 6.3 | 6.3 | |
| | Mesenteric LN | 7.1 | 5.4 | |
| | Gastrohepatic LN | 8.7 | 6.1 | |
| 0012 | Pancreas | 3.4 | 2.4 | 3.5 |
| | Right Upper Lung | 1.2 | 1.0 | |
| | Right Lower Lung | 0.9 | 0.7 | |
| | Left Upper Lung | 0.9 | 0.9 | |
| | Left Lower Lung | 1.3 | 1.5 | |
| | Uterus | 6.7 | 6.5 | |
| 0014 | Pancreas | 11.3 | 10.5 | 1.9 |
| | Lymph Nodes: | | | |
| | Supraclavicular | 9.2 | 9.6 | |
| | Right Mediastinal | 12.1 | 10.5 | |
| | Right Paratrachial | 4.7 | 13.2 | |
| | Right Hilar | 11.9 | 11.5 | |
| | Peripancreatic | 5.6 | 8.3 | |

TABLE 4-continued

CLN1 SINGLE-AGENT ACTIVITY BY PET

| Patient | Lesion Location | Baseline SUV* | Day 14 SUV | TTP (months) |
|---|---|---|---|---|
| 0015 | Pancreas | 11.3 | 10.1 | 2.5 |
|  | Iliac LN | 5.2 | 5.1 |  |

*SUV = standardized uptake value

Survival was significantly higher for patients with low plasma levels of CTGF at baseline (median overall survival of 10.4 months, n=7) than patients with a high levels of CTGF at baseline (median overall survival of 4.1 months, n=7) (p=0.0034). Data in Table 5.

TABLE 5

BASELINE PLASMA TOTAL CTGF AND SURVIVAL

| Baseline Plasma Total CTGF* | Modified ITT OS (mo)* | Risk Reduction (Cox) |
|---|---|---|
| ≤10 ng/Ml | 10.4 (n = 7) | 87% |
| >10 ng/mL | 4.1 (n = 7) |  |
| p-value | 0.0034 | 0.0120 |

*Baseline CTGF levels were not available for one patient. 10 ng/ml = median value.

An analysis of patient pharmacokinetic values indicate that patients that had the longest time to progression also had the highest level of circulating antibody at specific time points following administration. When measured at day 14 post administration ($C_{min}$), an antibody blood level of 80 µg/ml represented a threshold value above which surprisingly, patients had an increased time to disease progression. As shown in FIG. 1, the two best responding patients, patient 0006 and patient 0009 had mean $C_{min}$ of over 100 µg/ml and over 120 µg/ml, respectively. The mean $C_{min}$ was calculated from the individual $C_{min}$ for four successive antibody administrations. These two patients are both still alive further demonstrating that the increased circulating antibody levels are also associated with increased patient survival.

Increased time to disease progression is further associated with increased anti-CTGF antibody exposure expressed as the area under the curve (AUC). Analysis of the $AUC_{0-336\ hours}$ (the antibody exposure from time of administration to 14 days post-administration) for the third antibody administration demonstrated that an antibody exposure of at least 80,000 µg*h/ml is surprisingly associated with increased time to disease progression and increased survival. Patient 0006 had an $AUC_{0-336}$ of 102,000 gµ*h/ml, while patient 0009 had an $AUC_{0-336}$ of 95,700 µg*h/ml.

Figure 2:
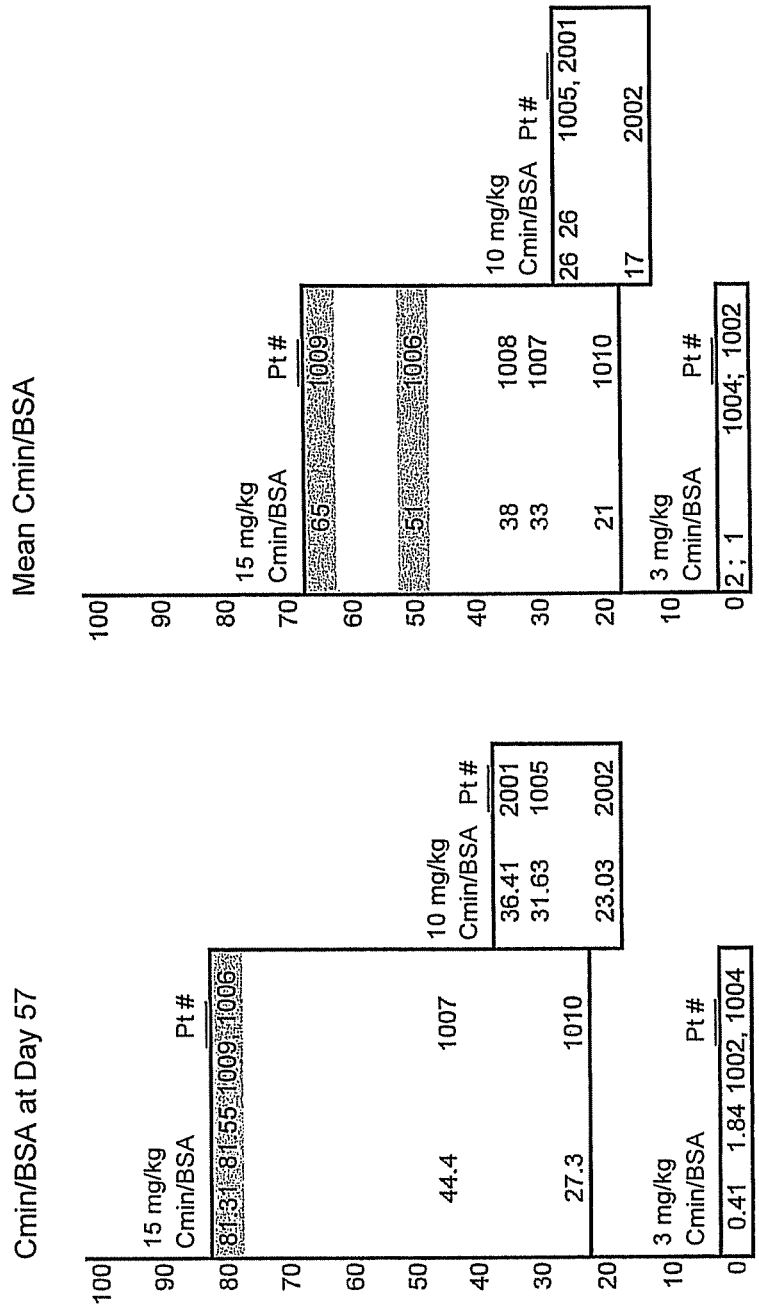
FIG. 2 illustrates the association between elevated $C_{min}$ levels and body surface area as expressed in µg/ml/m$^2$ and an increase in TTP seen in patients treated with the antibody CLN1.

An additional association that correlated with increased time to disease progression is the minimum level of circulating antibody present in a patient's blood a specific time point ($C_{min}$) divided by the patient's body surface area (BSA) to yield µg/ml/m². See FIG. 2. For patients 0006 and 0009 (1006 and 1009 in shaded portions of FIG. 2) both the $C_{min}/m^2$ at day 57, (82 µg/ml/m² and 81 µg/ml/m², respectively), corresponding to 14 days after the fourth CLN1 administration, and the mean $C_{min}/m^2$, calculated from the $C_{min}/m^2$ obtained 14 days after the administration of 4 sequential CLN1 administrations (51 µg/ml/m² and 65 µg/ml/m², respectively), are significantly higher than the other patients regardless of the administered antibody dose. These two patients have a surprising increase in both time to disease progression and survival. It appears that a $C_{min}$ mean level of circulating antibody per m² of the patient's body surface area of at least 50 µg/ml/m² is associated with increased survival. These data show that increased exposure to CLN1 is associated with improved patient outcomes. The patients with higher continuous drug exposure, in general, have longer TTP.

Example 2

Further Anti-CTGF Antibody Dose Escalation in Advanced Pancreatic Cancer

The encouraging data generated in the dose finding study above, particularly the increased tumor response with increased antibody dose that was not associated with an increase in the occurrence or severity of adverse events beyond what would normally be expected with gemcitabine and erlotinib administration, led to the study protocol being amended to test higher doses of the CLN1 antibody. Additional patients were treated with 25 mg/kg (n=8), 35 mg/kg (n=10), and 45 mg/kg (n=13). All patients further received gemcitabine and erlotinib as described above.

The administration of higher doses of anti-CTGF antibody was associated with continued tumor response. Additionally, the higher antibody doses did not increase the occurrence or severity of adverse events beyond what would normally be expected with gemcitabine and erlotinib. An examination of the accumulated patient data for dose cohorts 3 mg/kg to 45 mg/kg demonstrated a therapeutic threshold that was apparent at about 15 mg/kg and above. Using 15 mg/kg as a threshold, patients that were administered at least 15 mg/kg had a median OS of 8.6 months compared to a median OS of 6.6 months for patients administered less than 15 mg/kg. (See Table 6)

TABLE 6

Overall Survival

| Dose Group | n/event | median |
|---|---|---|
| Low <15 mg/kg | 7/7 | 6.6 |
| High ≥15 mg/kg | 59/23 | 8.6 |

Note:
The OS is based on Intent to Treat (ITT).
n is the number of subjects;
event is the number of deaths for OS.
OS is defined from time of signing of informed consent to the event.

Time to progression was also increased in patients that were administered at least 15 mg/kg. They had a median TTP of 7.5 months compared to a median TTP of 3.9 months for patients administered less than 15 mg/kg. (See Table 7)

TABLE 7

Time to Progression

| Dose Group | n/event | median |
|---|---|---|
| Low <15 mg/kg | 7/5 | 3.9 |
| High ≥15 mg/kg | 59/24 | 7.5 |

Note:
The TTP is based on ITT.
n is the number of subjects;
event is the number of progressors or deaths for TTP.
TTP is defined from time of signing of informed consent to the event.

Additionally, PFS was also increased in patients that were administered at least 15 mg/kg. They experienced a median PFS of 6.6 months compared to a median of PFS of 3.8 months for patients administered less than 15 mg/kg. (See Table 8)

TABLE 8

Progression-Free Survival

| Dose Group | n/event | median |
|---|---|---|
| Low <15 mg/kg | 7/7 | 3.8 |
| High ≥15 mg/kg | 59/32 | 6.6 |

Note:
The PFS is based on ITT.
n is the number of subjects;
event is the number of progressors or deaths for PFS.
PFS is defined from time of signing of informed consent to the event.

The increase in OS, TTP and PFS achieved with the addition of at least 15 mg/kg of an anti-CTGF antibody to treatment with gemcitabine and erlotinib are quite surprising in light of previous clinical trial results. Gemcitabine became the standard treatment for advanced pancreatic cancer in 1997 after demonstrating superior activity compared to 5-fluorouracil (5-FU), producing a median OS of 5.65 months versus a median of 4.41 months, respectively. (Burris H A, et al. *J Clin Oncol.* 1997; 15:2403-2413) Since then, ten phase III clinical trials of gemcitabine combined with other cytotoxic agents have not significantly improved upon the survival rate achieved with gemcitabine alone, demonstrating the intractable nature of the disease. (See Berlin J D et al. *J Clin Oncol.* 2002; 20:3270-3275; Rocha Lima C M et al. *J Clin Oncol.* 2004; 22:3776-3783; Louvet C et al. *J Clin Oncol.* 2005; 23: 3509-3516; Oettle H et al. *Ann Oncol.* 2005; 16:1639-1645; Abou Alfa G K et al. *J Clin Oncol.* 2006; 24:4441-4446; Poplin E et al. *J Clin Oncol.* 2006; 24:180s; Van Cutsem E et al. *J Clin Oncol.* 2009; 27:2231-2237; Benedetti P P A et al. *J Clin Oncol.* 2010; 28:3605-3610; Kindler H L et al. *J Clin Oncol.* 2010: 28:3617-3622; and Kindler H L et al. *Lancet Oncol.* 2011; 12:256-262). Similarly, three phase III clinical trials of gemcitabine combined with biologic agents have also failed to significantly improve upon the survival rate of gemcitabine alone. (See Van Cutsem E et al. *J Clin Oncol.* 2004; 22:1430-1438; Bramhall S R et al. *Br J Cancer.* 2002; 87:161-167; and Gilliam A D et al. *Expert Opin Bio Ther.* 2007; 7:397-404)

The only exception to the failure of gemcitabine-based combination treatment regimens in extending survival rates in a statistically significant manner was seen with the combination of gemcitabine and erlotinib, an oral HER1/EGFR tyrosine kinase inhibitor, where median OS was extended 0.33 months over gemcitabine alone (OS of 6.24 months and 5.91 months, respectively). The addition of erlotinib also extended PFS by 0.20 months over gemcitabine alone, (PFS of 3.75 months and 3.55 months, respectively).

The addition of an anti-CTGF antibody in the present study to gemcitabine and erlotinib combination therapy resulted in remarkable additional improvements of OS (2.0 month gain), TTP (3.6 month gain) and PFS (2.8 month gain) over that seen with gemcitabine and erlotinib combination therapy. Even more surprisingly, these gains were achieved without a concomitant increase in the occurrence or severity of adverse events beyond what would be expected with the use of gemcitabine and erlotinib. These results demonstrate the treatment with an anti-CTGF antibody is well tolerated. As of yet, no dose-limiting toxicity has been identified.

The use of at least 15 mg/kg of an anti-CTGF antibody was also associated with a marked reduction in the blood level of the tumor marker CA 19-9 in patients that expressed abnormally high amounts of the tumor marker, i.e., a baseline >100 U/ml. (Table 9) Almost half of the patients that received at least 15 mg/kg of anti-CTGF antibody experienced at least a 50% reduction in the blood level of the tumor marker, while almost a third experience a greater than 80% reduction. These results demonstrate the utility of using a tumor marker as a proxy for measuring a tumor response. The reduction in a tumor marker can also be used to titrate an antibody dose and is further beneficial in monitoring the treatment of a patient, particularly in cases where fibrosis and slow clearance of non-viable tumor prevent or impede assessment with other monitoring or imaging modalities.

TABLE 9

CA 19-9 Response*

| Dose Group | Total N | Percentage of Patients with Baseline CA19-9 >100** | Reduction from Baseline >50% | Reduction from Baseline >80% |
|---|---|---|---|---|
| Low <15 mg/kg | 7 | 4 | 1 (25%) | 0 |
| High ≥15 mg/kg | 41 | 25 | 12 (48%) | 8 (32%) |

Note:
CA 19-9 response is based on ITT.
*Response is defined as the largest reduction from baseline observed during the treatment period.
**Only subjects with baseline CA 19-9 >100 U/ml are included in the responder analyses.

Example 3

A newly diagnosed, chemotherapy naïve, patient with advanced metastatic, pancreatic cancer is treated with standard gemcitabine therapy (1000 mg/m$^2$/week, IV for 7 weeks followed by a week of rest, then weekly for 3 weeks, every 28 days) and an anti-CTGF antibody (CLN1) administered in two-week treatment cycles, without a rest period, independent of the gemcitabine treatment schedule. The total amount of anti-CTGF antibody (CLN1) to be administered per treatment cycle is determined by titration. An initial dose of 15 mg/kg is administered at the start of a first two-week treatment cycle. At the end of the two-week period, blood is drawn for the measurement of the antibody concentration that remains in circulation. The patient's blood antibody concentration is 132 µg/ml. This compares to a target antibody blood concentration of 150 µg/ml at 2 weeks post-administration. Therefore, the quantity of antibody administered at the start of the second treatment cycle is increased above 15 mg/kg to a level calculated to meet or exceed 150 µg/ml when a new blood sample is drawn at the end of the second treatment cycle. The increased quantity of antibody is calculated to compensate for the increased antibody clearance and reduced antibody half-life seen in this patient.

At the end of the second two-week period, blood is again drawn and assayed for antibody concentration. Following the adjustment in antibody dose, the patient's blood concentration of antibody is 187 µg/ml and therefore, exceeds the target concentration that is associated with increased survival and tumor response. The patient's next antibody dose is the same as the second antibody dose. Following this third dose, blood is again drawn at 14 days post-administration and the antibody concentration measured. The antibody concentration is 203 µg/ml and exceeds the target antibody blood level. The patient's next antibody dose and all subsequent antibody doses are held constant at the amount calculated for the second antibody dose. No further assays of blood antibody concentration are performed. The patient's cancer responds to the combined anti-CTGF antibody and gemcitabine treatment and the patient experiences an OS of 8.7 months, a TTP of 7.4 months and a PFS of 6.6 months. No additionally toxicity is noted with the addition of the anti-CTGF antibody compared to what would be expected with gemcitabine therapy alone, further demonstrating the benefit of this treatment modality.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of treating a human subject with pancreatic cancer and having a pretreatment CTGF blood level of ≤10 ng/ml comprising treating the subject with a therapeutic regimen comprising an effective quantity of a chemotherapy agent and an effective quantity of an anti-CTGF antibody to achieve a $C_{min}$ of the anti-CTGF antibody of at least 100 μg/ml in blood when measured about 14 days after administration, wherein the antibody is identical to the antibody produced by the cell identified by ATCC Accession No. PTA-6006, and wherein the treatment increases the overall survival of the subject more than the overall survival achieved by administering the chemotherapy agent alone.

2. The method of claim 1, wherein the chemotherapy agent is gemcitabine or erlotinib.

3. The method of claim 1, wherein the overall survival achieved is an increase of at least 1 month longer than the overall survival achieved with the chemotherapy agent alone.

* * * * *